US012767995B2

(12) United States Patent
Shao et al.

(10) Patent No.: US 12,767,995 B2
(45) Date of Patent: Oct. 20, 2026

(54) CATALYTIC AMPLIFICATION BY TRANSITION-STATE MOLECULAR SWITCHES FOR DIRECT AND SENSITIVE DETECTION OF SARS-CoV-2

(71) Applicant: National University of Singapore, Singapore (SG)

(72) Inventors: Huilin Shao, Singapore (SG); Noah Riandiputra Sundah, Singapore (SG); Auginia Natalia, Singapore (SG); Yu Liu, Singapore (SG)

(73) Assignee: National University of Singapore, Singapore (SG)

( * ) Notice: Subject to any disclaimer, the term of this patent is extended or adjusted under 35 U.S.C. 154(b) by 502 days.

(21) Appl. No.: 18/275,540

(22) PCT Filed: Jan. 24, 2022

(86) PCT No.: PCT/SG2022/050031
§ 371 (c)(1),
(2) Date: Aug. 2, 2023

(87) PCT Pub. No.: WO2022/169412
PCT Pub. Date: Aug. 11, 2022

(65) Prior Publication Data

US 2024/0043945 A1 Feb. 8, 2024

(30) Foreign Application Priority Data

Feb. 2, 2021 (SG) ........................... 10202101092X

(51) Int. Cl.
*B01L 3/00* (2006.01)
*C12Q 1/68* (2018.01)
*C12Q 1/682* (2018.01)
*C12Q 1/686* (2018.01)
*C12Q 1/70* (2006.01)

(52) U.S. Cl.
CPC ........ *C12Q 1/701* (2013.01); *B01L 3/502738* (2013.01); *B01L 2200/027* (2013.01); *B01L 2200/0647* (2013.01); *B01L 2200/16* (2013.01)

(58) Field of Classification Search
CPC .................. C12Q 1/6816; C12Q 1/701; C12Q 2521/101; C12Q 1/682; C12Q 2527/127
See application file for complete search history.

(56) References Cited

U.S. PATENT DOCUMENTS

| | | | |
|---|---|---|---|
| 10,041,111 | B2 | 8/2018 | Park et al. |
| 2021/0130870 | A1 | 5/2021 | Shao et al. |

FOREIGN PATENT DOCUMENTS

| | | | |
|---|---|---|---|
| CN | 111363860 | A | 7/2020 |
| CN | 111690717 | A | 9/2020 |
| WO | 2020/009660 | A1 | 1/2020 |

OTHER PUBLICATIONS

Y. Bai et al.; "Presumed Asymptomatic Carrier Transmission of COVID-19", JAMA, vol. 323, No. 14, Apr. 14, 2020, pp. 1406-1407 (2 pages).
J. P. Broughton et al.; "CRISPR-Cas12-based detection of SARS-CoV-2", Nature Biotechnology, vol. 38, Jul. 2020 pp. 870-874 (8 pages).
E. A. Bruce et al.; "Direct RT-qPCR detection of SARS-CoV-2 RNA from patient nasopharyngeal swabs without an RNA extraction step", PLOS Biology, bioRxiv, vol. 18, No. 10, Oct. 2, 2020 (14 pages).
L. J. Carter et al.; "Assay Techniques and Test Development for COVID-19 Diagnosis", ACS Central Science, vol. 6, Apr. 30, 2020, pp. 591-605 (15 pages).
Centers for Disease Control and Prevention; "CDC 2019—Novel Coronavirus (2019-nCoV) Real-Time RT-PCR Diagnostic Panel", Mar. 7, 2023 (80 pages).
A. W. H. Chin et al.; "Stability of SARS-CoV-2 in different environmental conditions", The Lancet Microbe, vol. 1, May 2020, p. e10 (1 page).
A. N. Cohen et al.; "Diagnosing COVID-19 infection: the danger of over-reliance on positive test results", medRxiv, Aug. 18, 2020 (11 pages).
C. Dang et al.; "Oligonucleotide Inhibitors of Taq DNA Polymerase Facilitate Detection of Low Copy Number Targets by PCR", J. Mol. Biol., vol. 264, No. 2, Nov. 29, 1996, pp. 268-278 (11 pages).
T. A. Duncombe et al.; "Microfluidics: reframing biological enquiry", Nature Reviews Molecular Cell Biology, vol. 16, Sep. 2015, pp. 554-567 (14 pages).
N. Garg et al.; "Rapid Immunodiagnostics of Multiple Viral Infections in an Acoustic Microstreaming Device with Serum and Saliva Samples", Lab Chip., vol. 19, No. 9, Apr. 23, 2019, pp. 1524-1533 (17 pages).

(Continued)

*Primary Examiner* — Barry A Chestnut
(74) *Attorney, Agent, or Firm* — Osha Bergman Watanabe & Burton LLP

(57) ABSTRACT

The present invention relates to the detection of target nucleic acids using enzyme-assisted nanotechnology. More specifically, the present invention provides a molecular nanotechnology in the form of a transition-state DNA-enzyme molecular switch and methods of use that enables direct and sensitive detection of viral RNA targets in native clinical samples. In one embodiment, the detection comprising steps of providing a composition comprising at least one DNA polymerase enzyme, at least one enhancer, and at least one DNA polymerase inhibitor, wherein the DNA polymerase inhibitor is recognized and bound by the DNA polymerase enzyme via its conserved region, and is complementary to a portion of the enhance via its variable region. In another embodiment, the detection method comprising steps of providing a signalling nanostructure and detecting signal development, wherein a change in the intensity of signal. In an alternative embodiment, the target nucleic acid is a SARS-CoV-2 polynucleotide.

20 Claims, 16 Drawing Sheets

Specification includes a Sequence Listing.

(56) References Cited

OTHER PUBLICATIONS

A. E. Gorbalenya et al.; "The species Severe acute respiratory syndrome-related coronavirus: classifying 2019-nCoV and naming it SARS-CoV-2", Nature Microbiology, vol. 5, Mar. 2020, pp. 536-544 (9 pages).
H. Hasegawa et al.; "Methods for Improving Aptamer Binding Affinity", Molecules, vol. 21, No. 421, Mar. 28, 2016 (15 pages).
H. Huang et al.; "COVID-19: A Call for Physical Scientists and Engineers", ACS Nano, vol. 14, Apr. 8, 2020, pp. 3747-3754 (8 pages).
N. R. Y. Ho et al.; "Visual and modular detection of pathogen nucleic acids with enzyme-DNA molecular complexes", Nature Communications, vol. 9, No. 3238, Aug. 13, 2018 (11 pages).
J. H. Jeong et al.; "Comparison of Sputum and Nasopharyngeal Swabs for Detection of Respiratory Viruses", Journal of Medical Virology, vol. 86, May 6, 2014, pp. 2122-2127 (6 pages).
M. R. Jones et al.; "Programmable materials and the nature of the DNA bond", Science, vol. 347, No. 6224, Feb. 20, 2015 (13 pages).
A. Ladha et al.; "A 5-min RNA preparation method for COVID-19 detection with RT-qPCR", medRxiv, May 8, 2020 (3 pages).
J. Li et al.; "Engineering nucleic acid structures for programmable molecular circuitry and intracellular biocomputation", Nature Chemistry, vol. 9, Sep. 25, 2017, pp. 1056-1067 (12 pages).
Y. Li et al.; "Multiplexed detection of pathogen DNA with DNA-based fluorescence nanobarcodes", Nature Biotechnology, vol. 23, Jun. 12, 2015, pp. 885-889 (5 pages).
Y. Li et al.; "Stability issues of RT-PCR testing of SARS-CoV-2 for hospitalized patients clinically diagnosed with COVID-19", Journal of Medical Virology, vol. 92, Mar. 22, 2020, pp. 903-908 (6 pages).
C. Z. J. Lim et al.; "Subtyping of circulating exosome-bound amyloid β reflects brain plaque deposition", Nature Communications, vol. 10, No. 1144, Mar. 8, 2019 (11 pages).
K. Okonechnikov et al.; "Unipro UGENE: a unified bioinformatics toolkit", Bioinformatics, vol. 28, No. 8, Feb. 24, 2012, pp. 1166-1167 (2 pages).
C. W. M. Ong et al.; "Epidemic and pandemic viral infections: impact on tuberculosis and the lung", Eurpean Respiratory Journal, vol. 56, No. 4, 2020 (26 pages).
C. W. M. Ong et al.; "Impact of the global COVID-19 outbreak on the management of other communicable diseases", International Journal of Tuberculosis and Lung Disease, vol. 24, Mar. 19, 2020, pp. 547-548 (2 pages).
Y. Pan et al.; "Viral load of SARS-CoV-2 in clinical samples", The Lancet, Infectious Diseases, vol. 20, No. 4, Apr. 2020, pp. 411-412 (2 pages).
C. Rothe et al.; "Transmission of 2019-nCoV Infection from an Asymptomatic Contact in Germany", The New England Journal of Medicine, vol. 382, No. 10, Mar. 5, 2020, pp. 970-971 (2 pages).
S. M. Shaffer et al.; "Multiplexed detection of viral infections using rapid in situ RNA analysis on a chip", Lab on a Chip, vol. 15, Jun. 16, 2015, pp. 3170-3182 (13 pages).
H. Shao et al.; "Chip-based analysis of exosomal mRNA mediating drug resistance in glioblastoma", Nature Communications, vol. 6, No. 6999, May 11, 2015 (9 pages).
P. Song et al.; "Programming bulk enzyme heterojunctions for biosensor development with tetrahedral DNA framework", Nature Communications, vol. 11, No. 838, Feb. 11, 2020 (10 pages).
N. R. Sundah et al.; "Barcoded DNA nanostructures for the multiplexed profiling of subcellular protein distribution", Nature Biomedical Engineering, vol. 3, Sep. 2019, pp. 684-694 (14 pages).
E. Surkova et al.; "False-positive COVID-19 results: hidden problems and costs", The Lancet, Respiratory Medicine, vol. 8, No. 12, Sep. 29, 2020, pp. 1167-1168 (3 pages).
M. Tokeshi et al.; "Continuous-Flow Chemical Processing on a Microchip by Combining Microunit Operations and a Multiphase Flow Network", Analytical Chemistry, vol. 74, No. 7, Apr. 1, 2002, pp. 1565-1571 (7 pages).
Y. Toyoshima et al.; SARS-CoV-2 genomic variations associated with mortality rate of COVID-19:, Journal of Human Genetics, vol. 65, Jul. 22, 2020, pp. 1075-1082 (8 pages).
C. B. F. Vogels et al.; "Analytical sensitivity and efficiency comparisons of SARS-CoV-2 RT-qPCR primer-probe sets", Nature Microbiology, vol. 5, Oct. 2020, pp. 1299-1305 (13 pages).
R. Weissleder et al.; "COVID-19 diagnostics in context", Science Translational Medicine, vol. 12, No. 546, eabc1931, Jun. 3, 2020 (5 pages).
O. I. Wilner et al.; "Enzyme cascades activated on topologically programmed DNA scaffolds", Nature Nanotechnology, vol. 4, Apr. 2009, pp. 249-254 (7 pages).
X. Wu et al.; "Exosome-templated nanoplasmonics for multiparametric molecular profiling", Science Advances, vol. 6, No. 19, eaba2556 , May 6, 2020 (11 pages).
H. Xu et al.; "An ultraportable and versatile point-of-care DNA testing platform", Science Advances, vol. 6, No. 17, eaaz7445, Apr. 22, 2020 (10 pages).
C. Yan et al.; "Rapid and visual detection of 2019 novel coronavirus (SARS-CoV-2) by a reverse transcription loop-mediated isothermal amplification assay", Clinical Microbiology and Infection, vol. 26, No. 6, Apr. 8, 2020, pp. 773-779 (7 pages).
E. C. Yeh et al.; "Self-powered integrated microfluidic point-of-care low-cost enabling (SIMPLE) chip", Science Advances, vol. 3, e1501645, Mar. 22, 2017 (11 pages).
V. Yelleswarapu et al.; "Mobile platform for rapid sub-picogram-per-milliliter, multiplexed, digital droplet detection of proteins", PNAS, vol. 116, Mar. 5, 2019, pp. 4489-4495 (7 pages).
C. Jiang et al.; "Multiplexed Profiling of Extracellular Vesicles for Biomarker Development", Nano-Micro Letters, vol. 14, No. 3, Dec. 2, 2021 (36 pages).
N.R. Sundah et al.; "Catalytic amplification by transition-state molecular switches for direct and sensitive detection of SARS-CoV-2", Science Advances, vol. 7, eabe5940, Mar. 17, 2021 (11 pages).
International Search Report issued in PCT/SG2022/050031 on Mar. 18, 2022 (6 pages).
Written Opinion of the International Searching Authority issued in PCT/SG2022/050031 on Mar. 18, 2022 (8 pages).
F. Wu et al.; "A new coronavirus associated with human respiratory disease in China"; Nature, vol. 579, No. 2, pp. 265-269; Mar. 12, 2020 (21 pages).
Office Action issued in counterpart Japanese Patent Application No. 2023-547029 mailed on Jan. 20, 2026 (12 pages).

Figure 4

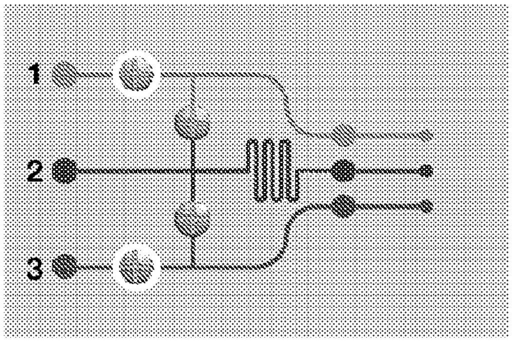

Step 1: Sample loading and target recognition

- Samples are introduced into the inlets, reconstituting the lyophilized reagents in the device.
- By opening the valves (white), samples flow into the detection chambers.

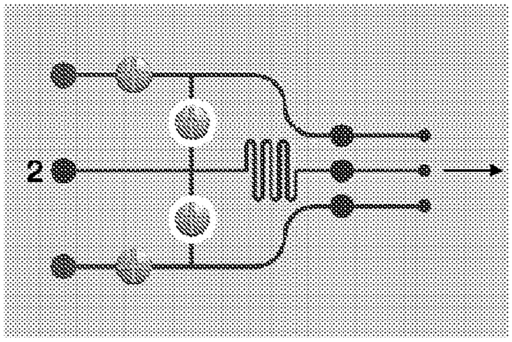

Step 2: Enzymatic amplification

- Excess reagent mixtures are removed via the waste outlet.
- By opening the valves (white), streptavidin-conjugated HRP is introduced through inlet 2.

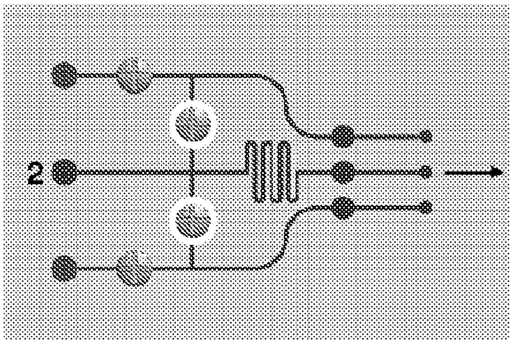

Step 3: Fluorescence detection

- Unbound HRP is removed and HRP substrate is introduced through inlet 2 into the detection chambers by opening the valves (white).
- On-chip, smartphone-based fluorescence measurements are performed to detect HRP substrate development.

SEQUENCE LISTING

```
<160> NUMBER OF SEQ ID NOS: 14

<210> SEQ ID NO 1
<211> LENGTH: 35
<212> TYPE: DNA
<213> ORGANISM: Artificial Sequence
<220> FEATURE:
<223> OTHER INFORMATION: SARS-CoV-2 S gene inhibitor

<400> SEQUENCE: 1

ttatttgact cctggtgatt caatgtacag tattg                              35


<210> SEQ ID NO 2
<211> LENGTH: 40
<212> TYPE: DNA
<213> ORGANISM: Artificial Sequence
<220> FEATURE:
<223> OTHER INFORMATION: SARS-CoV-2 S gene enhancer

<400> SEQUENCE: 2

aatcaccagg agtcaaataa cttctatgta aagcaagtaa                         40


<210> SEQ ID NO 3
<211> LENGTH: 35
<212> TYPE: DNA
<213> ORGANISM: Artificial Sequence
<220> FEATURE:
<223> OTHER INFORMATION: SARS-CoV-2 N gene inhibitor

<400> SEQUENCE: 3

aatccatgag cagtgctgac caatgtacag tattg                              35


<210> SEQ ID NO 4
<211> LENGTH: 40
<212> TYPE: DNA
<213> ORGANISM: Artificial Sequence
<220> FEATURE:
<223> OTHER INFORMATION: SARS-CoV-2 N gene enhancer

<400> SEQUENCE: 4

gtcagcactg ctcatggatt gttgcaattg tttggagaaa                         40


<210> SEQ ID NO 5
<211> LENGTH: 99
<212> TYPE: DNA
<213> ORGANISM: Artificial Sequence
<220> FEATURE:
<223> OTHER INFORMATION: Self-priming hairpin template

<400> SEQUENCE: 5
```

cggcgtacgt agagcgttga gcaggatgcc aacagtcgat caggacgagt gctaacgcat 60
tgtcgatagc tcagctgtct gagctatcga caatgcgtt 99

<210> SEQ ID NO 6
<211> LENGTH: 100
<212> TYPE: DNA
<213> ORGANISM: Artificial Sequence
<220> FEATURE:
<223> OTHER INFORMATION: Biotinylated dumbbell template

<400> SEQUENCE: 6
gtgcgtacat agatcgttat ctgtctaacg atctatgtac gcactcactc agctaacgca 60
ttgtcgatag ctcagctgtc tgagctatcg acaatgcgtt 100

<210> SEQ ID NO 7
<211> LENGTH: 60
<212> TYPE: DNA
<213> ORGANISM: Artificial Sequence
<220> FEATURE:
<223> OTHER INFORMATION: SARS-CoV-2 S gene synthetic target

<400> SEQUENCE: 7
gtttcaaact ttacttgctt tacatagaag ttatttgact cctggtgatt cttcttcagg 60

<210> SEQ ID NO 8
<211> LENGTH: 60
<212> TYPE: DNA
<213> ORGANISM: Artificial Sequence
<220> FEATURE:
<223> OTHER INFORMATION: 2 mismatch SARS-CoV-2 S gene synthetic target

<400> SEQUENCE: 8
gtttcaaact ttacttgctt tacatagaag ttctttgact cctgatgatt cttcttcagg 60

<210> SEQ ID NO 9
<211> LENGTH: 60
<212> TYPE: DNA
<213> ORGANISM: Artificial Sequence
<220> FEATURE:
<223> OTHER INFORMATION: 4 mismatch SARS-CoV-2 S gene synthetic target

<400> SEQUENCE: 9
gtttcaaact ttacttgctt tacatagaag ttcttggact catgatgatt cttcttcagg 60

<210> SEQ ID NO 10
<211> LENGTH: 60
<212> TYPE: DNA
<213> ORGANISM: Artificial Sequence
<220> FEATURE:
<223> OTHER INFORMATION: 6 mismatch SARS-CoV-2 S gene synthetic target

<400> SEQUENCE: 10
gtttcaaact ttacttgctt tacatagaag ctcttggaat catgatgatt cttcttcagg 60

<210> SEQ ID NO 11
<211> LENGTH: 60
<212> TYPE: DNA
<213> ORGANISM: Artificial Sequence
<220> FEATURE:
<223> OTHER INFORMATION: 8 mismatch SARS-CoV-2 S gene synthetic target

<400> SEQUENCE: 11
gtttcaaact ttacttgctt tacatagaag ctctgggaat catgatgagt cttcttcagg 60

-continued

```
<210> SEQ ID NO 12
<211> LENGTH: 60
<212> TYPE: DNA
<213> ORGANISM: Artificial Sequence
<220> FEATURE:
<223> OTHER INFORMATION: 10 mismatch SARS-CoV-2 S gene synthetic target

<400> SEQUENCE: 12

gtttcaaact ttacttgctt tacatagaag ctctgggaat caggattagt cttcttcagg     60


<210> SEQ ID NO 13
<211> LENGTH: 60
<212> TYPE: DNA
<213> ORGANISM: Artificial Sequence
<220> FEATURE:
<223> OTHER INFORMATION: 12 mismatch SARS-CoV-2 S gene synthetic target

<400> SEQUENCE: 13

gtttcaaact ttacttgctt tacatagaag ctctgggtat caggattagg cttcttcagg     60


<210> SEQ ID NO 14
<211> LENGTH: 15
<212> TYPE: DNA
<213> ORGANISM: Artificial Sequence
<220> FEATURE:
<223> OTHER INFORMATION: DNA polymerase inhibitor conserved sequence
      region

<400> SEQUENCE: 14

caatgtacag tattg                                                      15
```

CATALYTIC AMPLIFICATION BY TRANSITION-STATE MOLECULAR SWITCHES FOR DIRECT AND SENSITIVE DETECTION OF SARS-CoV-2

FIELD OF THE INVENTION

The present invention relates to the detection of nucleic acids using enzyme-assisted nanotechnology. More specifically, the present invention provides a molecular nanotechnology in the form of a transition-state DNA-enzyme molecular switch and methods of use that enables direct and sensitive detection of viral RNA targets in native clinical samples.

BACKGROUND OF THE INVENTION

The rapid global spread of coronavirus disease 2019 (COVID-19) has stretched the limits of healthcare resources [Huang H, et al., *ACS Nano.* 2020, 14: 3747-3754]. Person-to-person transmissions from infected individuals with no or mild symptoms have been widely reported [Bai W, et al., *JAMA.* 2020, 323(14): 1406-1407; Rothe C et al., *N Engl J Med.* 2020, 382: 970-871]. Aggressive testing for SARS-CoV-2, the causal pathogen of COVID-19 [Gorbalenya A E et al., *Nat Microbiol.* 2020, 5: 536-544], is important in controlling the disease spread and devising safety measures. To date, quantitative reverse transcription polymerase chain reaction (RT-qPCR) remains the primary assay for detecting SARS-CoV-2 [Carter L J et al., *ACS Cent Sci.* 2020, 6: 591-605]. Albeit its sensitive performance, the technology requires extensive sample preparation (e.g., RNA extraction), exquisite primer design, specialized instrument and trained personnel [Centers for Disease Control and Prevention, 2020, fdadotgov/media/134922/download]. These limitations not only result in a long assay turnaround time, but also hinder its large-scale implementation and adaptation in a rapidly evolving pandemic. Indeed, these shortcomings are particularly apparent, when challenged under the severe pressure of COVID-19; a global shortage of reagents and the emergence of new mutations and false negatives pose critical challenges for RT-qPCR-based detection [Bruce E A, et al., *bioRxiv.* 2020 doi.org/10.1101/2020.03.20.001008; Li Y et al., *J Med Virol.* 2020, 92: 903-908; Toyoshima Y et al., *J Hum Genet.* 2020, 65(12): 1075-1082]. Accurate, rapid and easy-to-use molecular diagnostic tests for SARS-CoV-2 are crucially needed across the globe [Weissleder R et al., *Sci Transl Med.* 2020, 12, eabc1931].

Molecular nanotechnology offers unparalleled precision and programmability to construct a variety of self-assembled functional nanostructures [Li J et al., *Nat Chem.* 2017, 9: 1056-1067; Li Y et al., *Nat Biotechnol.* 2005, 23: 885-889; Jones M R et al., *Science.* 2005, 347: 1260901; Sundah N R et al., *Nat Biomed Eng.* 2019, 3: 684-694]. These nanostructures can be designed as versatile, multi-function machines, which can not only recognize external stimuli, but also respond and actuate various activities [Wilner 01 et al., *Nat Nanotechnol.* 2009, 4: 239-254; Song P et al., *Nat Commun.* 2020, 11: 838]. We have previously developed a molecular nanotechnology platform for rapid detection of nucleic acids [Ho N R Y et al., *Nat Commun.* 2018, 9: 3238]. Instead of relying on the traditional approach of target amplification (as in conventional RT-qPCR), the technology detects through target hybridization. It leverages enzyme-DNA hybrid nanocomplexes as molecular switches; upon the direct binding of specific nucleic acids (even RNA targets), the nanocomplexes dissociate to activate strong enzymatic activity. Importantly, the technology is highly programmable; new assays can be readily developed by modifying the highly configurable nanocomplexes, without needing complex design of PCR primers and dedicated fluorescent probes (e.g., Taqman probes). Due to this unique sensing mechanism and high programmability, we thus envision that the technology could enable direct detection of SARS-CoV-2, bypassing many steps and challenges of PCR detection (e.g., reverse transcription and thermal cycling). Nevertheless, given that a significant proportion of COVID-19 patients are reported to have a very low viral load [Pan Y et al., *Lancet Infect Dis.* 2020, 20: 411-412], our previously developed assay, with a limit of detection of ~10 amol, would have a limited sensitivity to diagnose a broad spectrum of COVID-19 patients.

There is a need to bridge this gap in detection sensitivity.

SUMMARY OF THE INVENTION

Motivated by the multi-component nature of individual nanocomplexes, we reason that they can be tuned to establish highly responsive molecular switches. Specifically, the nanocomplex switches are self-assembled from multiple molecular constituents—Taq polymerase and distinct DNA strands—which exist in a dynamic equilibrium and exert different effects on overall switch characteristics. Through ratiometric tuning of these molecular constituents, we found that the most responsive state is a metastable state, where even trace amounts of target nucleic acids can readily activate the molecular switches to induce strong enzymatic activity. Leveraging molecular switches in this hyper-responsive state, which we call the transition state, we developed a highly sensitive and direct nucleic acid detection assay for SARS-CoV-2. The technology, termed catalytic amplification by transition-state molecular switch (CATCH), benefits from dual catalytic amplification: its transition-state molecular switches are readily activated upon the direct binding of even sparse amounts of viral RNA targets to liberate substantial enzymatic activity; this switch activation further recruits additional enzymatic cascades to transduce strong signal output.

Harnessing its hyper-responsiveness, CATCH achieves superior performance. It enables sensitive and specific detection of RNA targets, against a complex biological background, and reports a limit of detection (LOD) of ~8 copies of target per μl, which is >10,000-fold more sensitive than our previous platform. The detection is also direct and rapid; the entire assay can be completed in <1 hour at room temperature and can be applied to a variety of sample types (e.g., purified RNA as well as complex clinical samples), bypassing all steps of conventional RT-qPCR (i.e., RNA extraction, reverse transcription and thermal cycling amplification). Importantly, CATCH enables versatile assay implementation. To support different diagnostic needs, the assay can be implemented in a 96-well format for high-throughput analysis and as a miniaturized microfluidic cartridge for portable smartphone-based measurement. When applied for clinical detection of SARS-CoV-2, CATCH demonstrated accurate and sensitive detection in both extracted RNA samples as well as inactivated patient swabs.

In a first aspect of the invention there is provided a method of detecting target polynucleotides in a sample, comprising the steps of:

(a) providing a sample comprising polynucleotides;

(b) providing a composition comprising at least one DNA polymerase enzyme, at least one enhancer, and at least one DNA polymerase inhibitor, wherein;

i) the enhancer is a polynucleotide comprising a sequence that is complementary to a target polynucleotide sequence;

ii) the DNA polymerase inhibitor is a polynucleotide comprising a conserved region and a variable region, wherein the conserved region is recognized and bound by the DNA polymerase enzyme, and the variable region is complementary to a portion of the enhancer;

iii) complementary sequences of the variable region of the inhibitor and enhancer form a duplexed inhibitory DNA complex which inhibits DNA polymerase activity;

iv) the composition comprises an amount of inhibitory complex that has been determined to have the fastest response and/or highest signal-to-noise ratio, for example by using 1$^{st}$ (first) derivative of a titration curve of inhibitory complex v polymerase activity and/or by using 1$^{st}$ (first) derivative of a titration curve of ratios of enhancer:inhibitor;

(c) contacting the sample comprising nucleic acid with the composition of (b), wherein target polynucleotide binding to:

(i) the enhancer sequence region of the duplex in (b) displaces the inhibitor, thereby releasing and activating the DNA polymerase;

(d) providing a signalling nanostructure that is reactive to active DNA polymerase enzyme from step (c);

(e) contacting the signalling nanostructure with active DNA polymerase enzyme from step (c);

(f) detecting signal development, wherein a change in the intensity of signal indicates the presence of target nucleic acid in the sample when using composition (b).

In some embodiments the signalling nanostructure in d) comprises:

i) a self-priming portion responsive to the DNA polymerase enzyme, whereby in the presence of labelled oligonucleotides (dNTPs) and signal development reagents, the activated DNA polymerase enzyme adds labelled oligonucleotides to the signalling nanostructure and the signal development reagents bind to the labelled oligonucleotides incorporated into the self-primed portion; or ii) a self-priming exonuclease dumbbell nanostructure responsive to DNA polymerase enzyme exonuclease activity, wherein activated DNA polymerase enzyme removes labelled dNTPs from the dumbbell signalling nanostructure.

It would be understood that detection of target nucleic acid in the sample using signalling nanostructure i) is indicated by an increase in signal intensity, whereas the signalling nanostructure in ii) comprises a signal capacity that is reduced in the presence of activated DNA polymerase enzyme.

In some embodiments, the method further comprises;

(g) diagnosing the patient with the disease when presence of target nucleic acid in the sample is detected.

In some embodiments, the DNA polymerase inhibitor conserved sequence region comprises the nucleic acid sequence set forth in SEQ ID NO: 14; 5'-CAATGTACAGT-ATTG-3'.

In some embodiments, the amount of inhibitory complex in the composition is in the range of 20 nM to 60 nM and/or the enhancer to inhibitor ratio in the composition is less than 1:1, preferably in the range of 0.3:1 to 0.6:1.

In some embodiments, the enhancer is at least one nucleotide longer than the inhibitor duplex region.

In some embodiments, the enhancer is about 35 to 45, preferably about 40, nucleotides in length.

In some embodiments, about half of the length of the enhancer oligonucleotide forms the inhibitor-enhancer duplex and about half forms an overhang segment.

In some embodiments, the self-priming portion of the signalling nanostructure comprises the nucleic acid sequence set forth in SEQ ID NO: 5: 5'-CGGCGTACGTAGAGCGTTGAGCAGGATGC-CAACAGTCGATCAGGACGAGTGCTAACG CAT-TGTCGATAGCTCAGCTGTCTGAGC-TATCGACAATGCGTT-3'.

In some embodiments, the dNTP label is biotin.

In some embodiments, the signalling dumbbell nanostructure comprises the nucleic acid sequence set forth in SEQ ID NO: 6: 5'-GTGCGTACATAGATCGTTATCTGTC TAAC-GATCTATGTACGCACTCACTCAGCTAACGCAT-TGTCGATAGCTCAGCTGTCTGAG CTATCGACAATGCGTT-3'.

In some embodiments, the signal development reagents comprise a fusion protein comprising avidin or a derivative thereof and an enzyme, selected from a group comprising but not limited to HRP, beta-lactamase, amylase, beta-galactosidase, and respective substrates selected from a group comprising but not limited to DAB, TMB, ABTS, ADHP, nitrocefin, luminol, starch and iodine, wherein signals can be measured and quantified as but not limited to colour, fluorescence, luminescence or electrochemical changes.

In some embodiments, the target is at least one nucleic acid associated with a non-human or human disease, genetic variants, forensic, strain identification, environmental and/or food contamination.

In some embodiments, the target is at least one pathogen polynucleotide.

In some embodiments, the target is a SARS-CoV-2 polynucleotide, preferably wherein the inhibitor and enhancer polynucleotides are selected from those listed in Table 1. In some embodiments, the inhibitor and enhancer polynucleotides are selected from the group comprising SEQ ID NO: 1, SEQ ID NO: 2, SEQ ID NO: 3 and SEQ ID NO: 4.

In some embodiments, the method according to any aspect of the invention is performed in a multi-well format, a microfluidic device or lateral flow device.

In some embodiments, the method steps are performed at a temperature in the range from 16° C. to 40° C., preferably at room temperature.

A third aspect of the invention provides a device comprising:

(i) composition b) comprising at least one DNA polymerase enzyme and at least one inhibitory DNA complex, as defined in any aspect of the invention, at a 1$^{st}$ (first) location;

(ii) signalling nanostructures comprising a self-priming portion responsive to active DNA polymerase enzyme, as defined in any aspect of the invention, attached at a 2$^{nd}$ (second) location; and (iii) an intermediate stage for mixing of said detection nanostructures with sample nucleic acid to release active enzyme to said 2$^{nd}$ (second) location.

In some embodiments, the device is selected from a group comprising a multi-well plate, a microfluidic device and a lateral flow device.

In some embodiments, the device is a microfluidic device comprising:

(i) an inlet at a 1$^{st}$ (first) location, to introduce test sample, positive and negative controls, and reconstitute the lyophilized reagents in the device including at least one DNA polymerase enzyme, at least one enhancer, and at least one DNA polymerase inhibitor as defined in any aspect of the invention;

(ii) a detection chamber comprising signalling nanostructures at a $2^{nd}$ (second) location, in fluid connection with said $1^{st}$ (first) location, to receive activated DNA polymerase enzyme;

(iii) valves between said $1^{st}$ (first) and $2^{nd}$ (second) locations to control flow of sample and reagents;

wherein, when the device is assembled and in use, there is fluidic flow from the sample inlet to an outlet.

Examples of a suitable microfluidic devices are shown in FIG. 3 and FIG. 4.

A fourth aspect of the invention provides a nucleic acid detection kit comprising;

(a) a composition comprising at least one DNA polymerase enzyme and at least one inhibitory DNA complex, wherein the inhibitory DNA complex comprises a DNA polymerase enzyme-specific DNA inhibitor and an enhancer polynucleotide, wherein the inhibitor has a conserved sequence region and a variable sequence region, wherein the variable sequence region comprises an overhang segment which is at least 7 nucleotides complementary to, and forms a duplex with, a portion of the enhancer polynucleotide, wherein the enhancer polynucleotide is at least one nucleotide longer than the inhibitor-enhancer duplex and has more than 7 nucleotides complementary to a target polynucleotide; optionally (b) a signalling nanostructure that is reactive to active DNA polymerase enzyme; optionally (c) labelled nucleotides (dNTPs) and signal development reagents, wherein active DNA polymerase enzyme adds labelled nucleotides to the signalling nanostructure and the signal development reagents bind to the labelled nucleotides incorporated into the self-primed portion.

In some embodiments the signalling nanostructure in b) comprises:

i) a self-priming portion responsive to the DNA polymerase enzyme, whereby in the presence of labelled oligonucleotides (dNTPs) and signal development reagents, the activated DNA polymerase enzyme adds labelled oligonucleotides to the signalling nanostructure and the signal development reagents bind to the labelled oligonucleotides incorporated into the self-primed portion; or ii) a self-priming exonuclease dumbbell nanostructure responsive to DNA polymerase enzyme exonuclease activity, wherein activated DNA polymerase enzyme removes labelled dNTPs from the dumbbell signalling nanostructure.

In some embodiments, components (a) to (c) are as defined according to any aspect of the invention.

In some embodiments, the nucleic acid detection kit is configured into a device according to any aspect of the invention.

In some embodiments, at least one of the inhibitor polynucleotides and/or enhancer polynucleotides is structurally and/or chemically modified from its natural nucleic acid.

In some embodiments, said structural and/or chemical modification is selected from the group comprising the addition of tags, such as fluorescent tags, radioactive tags, biotin, a 5' tail, the addition of phosphorothioate (PS) bonds, 2'-O-Methyl modifications and/or phosphoramidite C3 Spacers during synthesis.

BRIEF DESCRIPTION OF THE FIGURES

FIG. 4 shows operation of the microfluidic CATCH platform. Valves to be opened in each step are outlined.

DETAILED DESCRIPTION OF THE INVENTION

Bibliographic references mentioned in the present specification are for convenience listed in the form of a list of references and added at the end of the examples. The whole content of such bibliographic references is herein incorporated by reference. Any discussion about prior art is not an admission that the prior art is part of the common general knowledge in the field of the invention.

Definitions

Unless defined otherwise, all technical and scientific terms used herein have the same meaning as is commonly understood by one of skill in the art to which the invention belongs. Certain terms employed in the specification, examples and appended claims are collected here for convenience.

It must be noted that as used herein and in the appended claims, the singular forms "a," "an," and "the" include plural reference unless the context clearly dictates otherwise. Thus, for example, a reference to "a target sequence" includes a plurality of such target sequences, and a reference to "an enzyme" is a reference to one or more enzymes and equivalents thereof known to those skilled in the art, and so forth.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material.

As used herein, the term "inhibitory complex" refers to a duplex of inhibitor polynucleotide and enhancer polynucleotide which inactivates DNA polymerase bound to it.

As used herein, the term "DNA polymerase inhibitor" or "inhibitor" is a polynucleotide comprising a conserved region and a variable region, wherein the conserved region is recognized and bound by the DNA polymerase enzyme, and the variable region is complementary to a portion of the enhancer polynucleotide.

As used herein, the term "enhancer" refers to a polynucleotide comprising a sequence that is complementary to a target polynucleotide sequence, of which a portion is involved in forming a duplex with complementary sequences of the variable region of the DNA polymerase inhibitor and a portion is involved in an overhang. Preferably, the enhancer is about 40 nucleotides in length, that is complementary to a target polynucleotide sequence, and 20 of the 40 nucleotides form the duplex with the inhibitor and 20 nucleotides of the 40 nucleotides form an overhang. Thus, the inhibitor and enhancer form a duplexed inhibitory DNA complex which inhibits DNA polymerase activity until such time as the enhancer is displaced upon duplex formation with target polynucleotide sequence.

Figure 2:
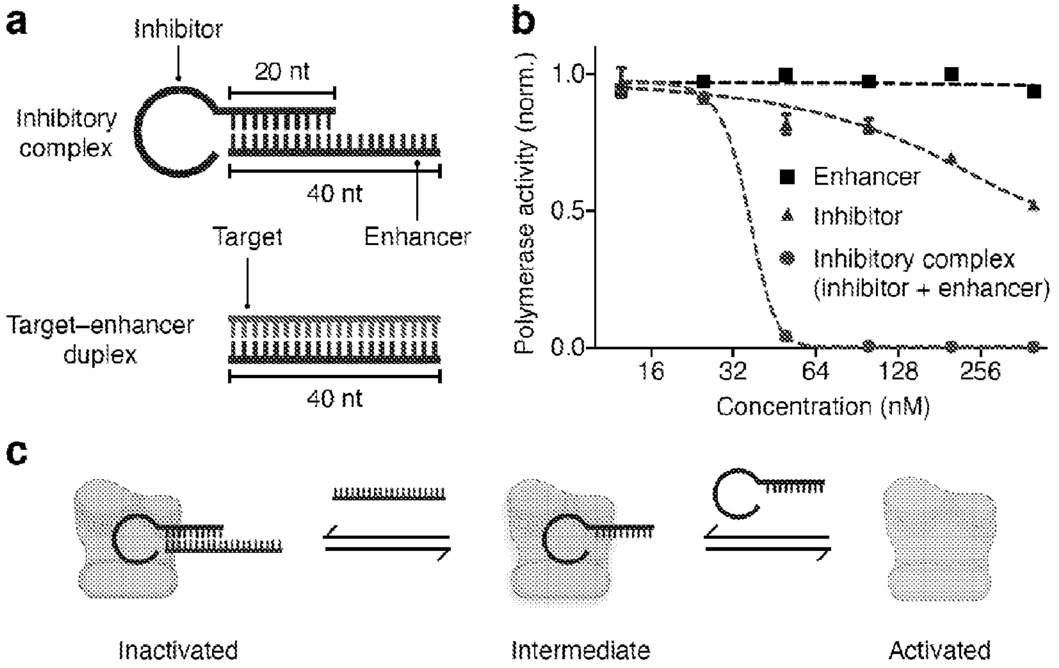
FIG. 2 shows polymerase activity of multicomponent molecular switches. (a) Schematic representation of the inhibitory complex. The complex consists of an inhibitor and an enhancer strand. While only half of the enhancer strand (20 nucleotides) can hybridize with the inhibitor strand, it is designed to be fully complementary (all 40 nucleotides) with the target, making the formation of the target-enhancer duplex thermodynamically favored. Within the inhibitory complex, half of the enhancer strand remains single-stranded so that its displacement by the target is kinetically favored. (b) Inhibitory effects of the different molecular switch constituents on polymerase activity. The inhibitor strand alone weakly decreases the polymerase activity, while the addition of the enhancer strand strongly inhibits the polymerase activity. The enhancer strand by itself does not demonstrate any appreciable inhibitory effect. (c) Schematic representation of the dynamic equilibrium between different forms of the molecular switches (i.e., inactivated, intermediate and activated). All measurements in (b) were performed in triplicate, and the data are presented as mean±s.d.
Figure 6:
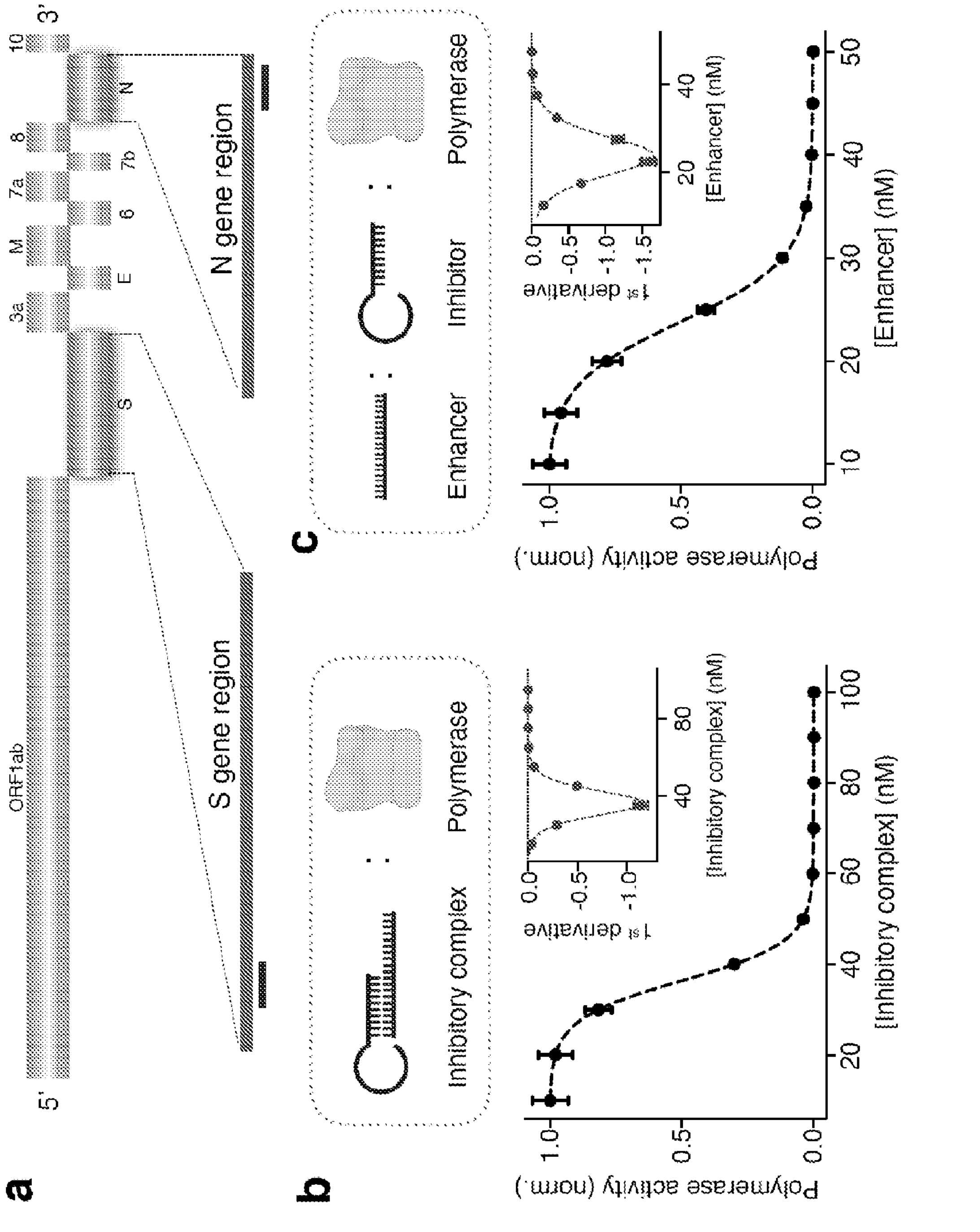
FIG. 6 shows hyper-responsive molecular switches for SARS-CoV-2 detection. (a) Map of the SARS-CoV-2 genome. Molecular switches are designed to recognize the spike (S) gene and the nucleocapsid (N) gene. Enhancer strands of respective molecular switches are represented by red rectangles. Not drawn to scale. (b) Switch responsiveness to inhibitory complex. To a fixed concentration of polymerase, we added a varying concentration of inhibitory complex (with the enhancer:inhibitor ratio kept at 1:1) and measured the resultant polymerase activity. Inset shows the first derivative plot for visualization of switch responsiveness to inhibitory complex. Switch composition at the vertex was deemed the most responsive and selected for further optimization. (c) Determination of the transition state. We further varied the concentration of the enhancer strand with fixed inhibitor strand concentration, and measured the resultant polymerase activity. Inset shows the first derivative plot for visualization of switch responsiveness to enhancer strand. We defined the transition state as the vertex composition. (d) Performance of the molecular switches. The closed-, open- and transition-state molecular switches were incubated with on-target and off-target sequences. The transition-state molecular switches exhibited significant polymerase activation with target binding while maintaining a low background. (e) Activation kinetics. The transition-state molecular switches achieved fast activation upon incubation with SARS-CoV-2 S gene target. Different molecular switches in d and e were prepared at the following representative compositions (inhibitor and enhancer strand, respectively): open state, 1 nM and 1 nM; transition state, 36 nM and 24 nM; closed state, 100 nM and 100 nM. All measurements were performed in triplicate, and the data in b-e are presented as mean±s.d. (**$P<0.0001$, *$P<0.005$, n.s., not significant, Student's t-test).
Figure 6:
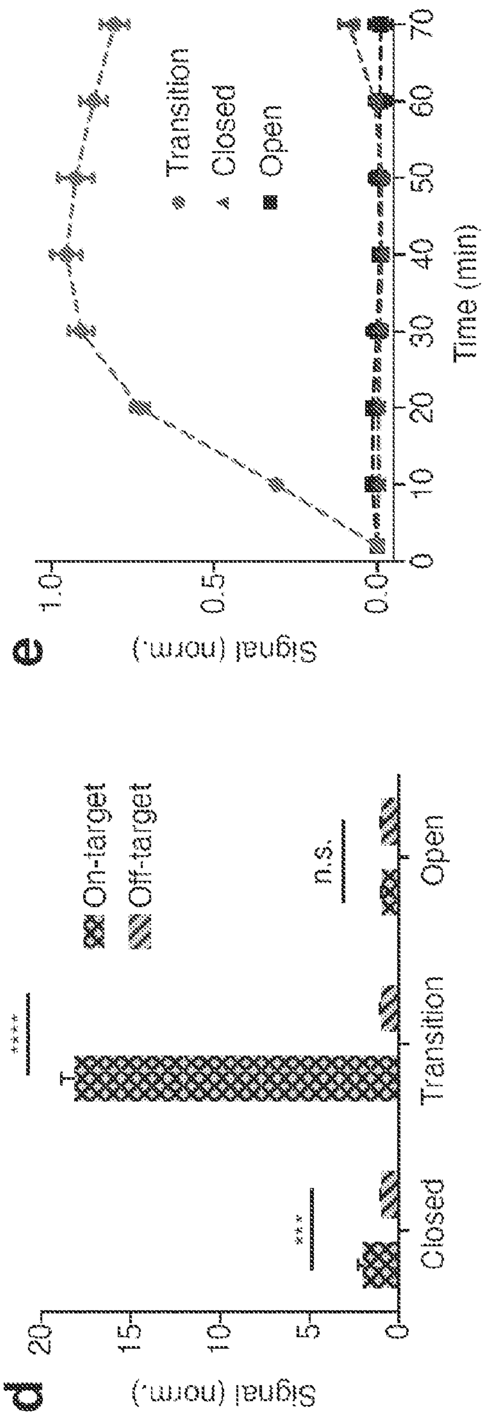
Figure 7:
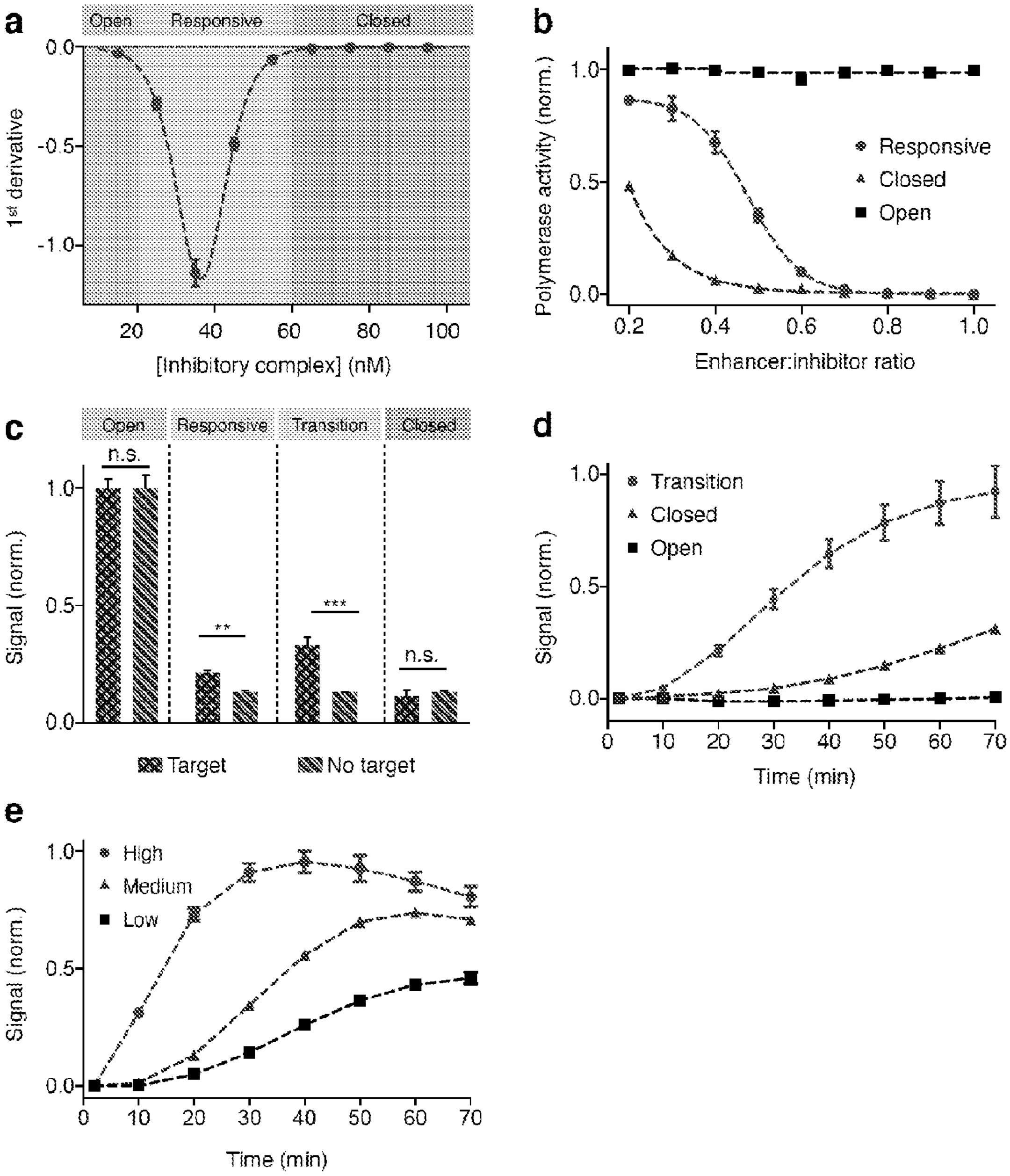
FIG. 7 shows performance characterization of the transition-state molecular switches. (a) First derivative plot of the inhibition curve to illustrate switch responsiveness to inhibitory complex. Molecular switches were prepared with a varying concentration of the inhibitory complex. Based on the resultant changes in polymerase activity, we categorized molecular switches into three groups: open, responsive, and closed. In the responsive range, molecular switches are responsive to changes in the inhibitory complex concentration. When the inhibitory complex concentration is above this range, molecular switches are in the closed state, where most switches are inactivated. When the inhibitory complex concentration is below this range, molecular switches are in the open state, where switches are predominantly activated. (b) Perturbation of the responsive-, closed- and open-state molecular switches. Molecular switches were perturbed by reducing the ratio of enhancer:inhibitor. Responsive-state molecular switches could not only react to a broader range of perturbations, but also respond with bigger changes in their polymerase activity. (c) Signal evaluation of the transition-state molecular switches. Molecular switches of different states were incubated with or without target for 30 minutes at room temperature and the resultant polymerase activity was measured. The transition-state molecular switches showed further signal improvement over the responsive-state switches, while the closed- and open-state switches failed to produce any distinguishable signal. (d) Activation kinetics. When incubated with SARS-CoV-2 N-gene target at room temperature, the transition-state molecular switches achieved the fastest activation kinetics. (e) Signal generation kinetics. Transition-state molecular switches were activated with different target concentrations. Higher target concentration results in faster signal generation. Different molecular switches in (c)-(e) were prepared at the following representative compositions (inhibitor and enhancer strand, respectively): open state, 1 nM and 1 nM; transition state, 36 nM and 24 nM; closed state, 100 nM and 100 nM. All measurements were performed in triplicate and the data are presented as mean±s.d. (*$P<0.005$, $P<0.01$, n.s., not significant, Student's t-test).

As used herein, the term "transition state" refers to an optimum inhibitor complex:DNA polymerase ratio which is further optimized in respect of enhancer:inhibitor ratio (see, for example FIG. 2c, FIG. 6 and FIG. 7). Through this optimization, the transition state is defined as the vertex on the first derivative inhibition plot (FIG. 2c, inset). This identified transition state demonstrates optimized responsiveness, producing the largest increase in polymerase activity, while the "open-" and "closed-state" switches failed to produce any distinguishable signal (FIG. 7c). In the so-called closed state, most of the molecular switches are fully inactivated, through polymerase binding with excess inhibitory complexes; turning on the polymerase activity thus requires a large amount of RNA targets. In the open state, most of the molecular switches are fully activated; turning on additional polymerase activity amidst a high initial background results in a low net signal. In the transition state, different forms of molecular switches (i.e., inactivated, intermediate and activated) (FIG. 2c) exist in a delicate dynamic equilibrium; a small amount of target molecules can readily shift the equilibrium to favor the formation of more activated switches, thereby triggering a large increase in overall polymerase activity.

The term "sample," as used herein, is used in its broadest sense. For example, a biological sample suspected of containing SARS-CoV-2 genome sequences may comprise a bodily fluid; an extract from a cell, chromosome, organelle, or membrane isolated from a cell; a cell; genomic DNA, RNA, or cDNA (in solution or bound to a solid support); a tissue; a tissue print; and the like.

It would be understood that oligonucleotides used in the present invention may be structurally and/or chemically modified to, for example, prolong their activity in samples potentially containing nucleases, during performance of methods of the invention, or to improve shelf-life in a kit. Thus, the inhibitor and/or enhancer and/or signalling nanostructure or any oligonucleotide primers or probes used according to the invention may be chemically modified. In some embodiments, said structural and/or chemical modifications include the addition of tags, such as fluorescent tags, radioactive tags, biotin, a 5' tail, the addition of phosphorothioate (PS) bonds, 2'-O-Methyl modifications and/or phosphoramidite C3 spacers during synthesis.

For example, the signalling oligonucleotide was modified for attachment chemistry with a 5' thiol group. Other attachment modifications can be made on the 5' end such as amino, acryldite, azide, etc.

The term "comprising" as used in the context of the invention refers to where the various components, ingredients, or steps, can be conjointly employed in practicing the present invention. Accordingly, the term "comprising" encompasses the more restrictive terms "consisting essentially of" and "consisting of." With the term "consisting essentially of" it is understood that the phenotypic features of the present invention "substantially" comprise the indicated features as "essential" element.

EXAMPLES

Example 1

Material and Methods

Molecular Switch Design and Preparation.

All oligonucleotide sequences can be found in Table 1 and were purchased from Integrated DNA Technologies (IDT). Genome sequences of SARS-CoV-2 (NC_045512), SARS-CoV (FJ882957), MERS (NC_019843), dengue virus (NC_001477) and influenza A subtype H1N1 virus (strain A/California/07/2009(H1N1), NC_026431-NC_026438) were obtained from NCBI RefSeq. Multiple sequence alignment was performed using the UGENE suite of tools [Okonechnikov K et al., *Bioinformatics.* 2012, 28:1166-1167]. To prepare molecular switches, we mixed inhibitor and enhancer oligonucleotides (Table 1, IDT) in a reaction buffer made up of 50 mM NaCl, 1.5 mM $MgCl_2$, and 50 mM Tris-HCl (pH 8.5). The mixture was incubated at 95° C. for 5 min and slowly cooled at 0.1° C./s until the reaction reached 25° C. to form the inhibitory complex. Taq DNA polymerase (Promega) was then added to form the complete molecular switch.

TABLE 1

| Oligonucleotide sequences. | |
|---|---|
| Molecular switches | |
| SARS-COV-2<br>S gene inhibitor | TTATTTGACTCCTGGTGATTCAATGTACAGTATTG<br>SEQ ID NO: 1 |
| SARS-COV-2<br>S gene enhancer | AATCACCAGGAGTCAAATAACTTCTATGTAAAGCAAGTAA<br>SEQ ID NO: 2 |
| SARS-COV-2<br>N gene inhibitor | AATCCATGAGCAGTGCTGACCAATGTACAGTATTG<br>SEQ ID NO: 3 |
| SARS-COV-2<br>N gene enhancer | GTCAGCACTGCTCATGGATTGTTGCAATTGTTTGGAGAAA<br>SEQ ID NO: 4 |
| Signalling oligonucleotides | |
| Self-priming hairpin<br>template | C**GG**C**G**TAC**G**TA**G**A**G**C**G**TT**G**A**G**CA**GG**AT**G**CCAACA**G**TC**G**ATCA**GG**<br>AC**G**A**G**T**G**CTAACGCATTGTCGATAGCTCAGCTGTCTGAGCTATCG<br>ACAATGCGTT<br>SEQ ID NO: 5 |
| Biotinylated dumbbell<br>template | **GTGCGTACATAGATCGTTA**TCTGTCTAACGATCTATGTACGCACT<br>CACTCAGCTAACGCATTGTCGATAGCTCAGCTGTCTGAGCTATCG<br>ACAATGCGTT<br>SEQ ID NO: 6 |

TABLE 1-continued

| Oligonucleotide sequences. | |
|---|---|
| Mismatch analysis | |
| SARS-COV-2 S gene synthetic target | GTTTCAAACTTTACTTGCTTTACATAGAAGTTATTTGACTCCTGGT GATTCTTCTTCAGG SEQ ID NO: 7 |
| 2 mismatch SARS-COV-2 S gene synthetic target | GTTTCAAACTTTACTTGCTTTACATAGAAGTTCTTTGACTCCTGAT GATTCTTCTTCAGG SEQ ID NO: 8 |
| 4 mismatch SARS-COV-2 S gene synthetic target | GTTTCAAACTTTACTTGCTTTACATAGAAGTTCTTGGACTCATGAT GATTCTTCTTCAGG SEQ ID NO: 9 |
| 6 mismatch SARS-COV-2 S gene synthetic target | GTTTCAAACTTTACTTGCTTTACATAGAAGCTCTTGGAATCATGAT GATTCTTCTTCAGG SEQ ID NO: 10 |
| 8 mismatch SARS-COV-2 S gene synthetic target | GTTTCAAACTTTACTTGCTTTACATAGAAGCTCTGGGAATCATGAT GAGTCTTCTTCAGG SEQ ID NO: 11 |
| 10 mismatch SARS-COV-2 S gene synthetic target | GTTTCAAACTTTACTTGCTTTACATAGAAGCTCTGGGGAATCAGGAT TAGTCTTCTTCAGG SEQ ID NO: 12 |
| 12 mismatch SARS-COV-2 S gene synthetic target | GTTTCAAACTTTACTTGCTTTACATAGAAGCTCTGGGGTATCAGGAT TAGGCTTCTTCAGG SEQ ID NO: 13 |

Bolded nucleotides indicate possible sites of biotin incorporation/removal.

Underlined nucleotides indicate mismatches.

Transition-State Characterization.

To identify various states of the molecular switch, we varied the ratio of its constituents, first with the inhibitor and enhancer strand at 1:1 ratio, then at varying ratios of these two components. The resultant polymerase activity was measured through 5' exonuclease degradation of fluorescent signalling probe. Briefly, equimolar amounts of fluorescent probe, template and primer (IDT) were mixed with deoxynucleotide triphosphates (dNTPs, Thermo Scientific) in the reaction buffer. The mixture was incubated at 95° C. for 5 min and slowly cooled to 25° C. at 0.1° C./s. Molecular switches were then added to the probe mixture and incubated at 25° C. while fluorescence readings were taken. Based on the observed changes in polymerase activity, we defined the different states of molecular switches: the open state is where the inhibitory complex is lacking (<20 nM), the closed state is where the inhibitory complex is in excess (>60 nM) and the transition state is the most responsive state (i.e., the vertex of the first derivative of the inhibition curve, where a small change in the switch composition would result in the largest change in polymerase activity). To characterize the responsiveness of the different switch states to nucleic acid targets, we prepared switches at the following representative composition and incubated the switches with target oligonucleotides: open state, 1 nM of inhibitor strand and 1 nM of enhancer strand; closed state, 100 nM of inhibitor strand and 100 nM of enhancer strand; and the transition state, 36 nM of inhibitor strand and 24 nM of enhancer strand. All experiments were also performed with scrambled oligonucleotides to determine background off-target signal.

Immobilization of Signalling Oligonucleotides.

Figure 9:
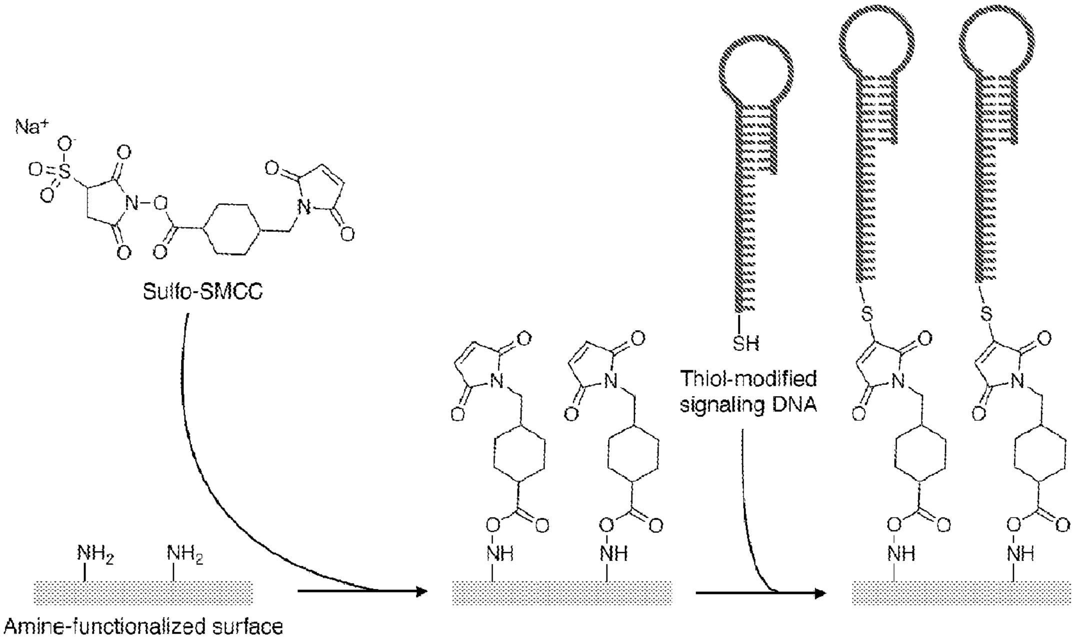
FIG. 9 shows immobilization of signalling oligonucleotides. The inventors first functionalized different sensor surfaces with amine groups. Specifically, for the 96-well plate, bovine serum albumin (BSA) was coated onto the plate as an amine-rich protein scaffold; for the microfluidic device, (3-aminopropyl)triethoxysilane (APTES) was applied. Primary amines were then activated by incubating with sulfosuccinimidyl 4-(N-maleimidomethyl)cyclohexane-1-carboxylate (sulfo-SMCC). Separately, thiol-modified signalling oligonucleotides were activated by reducing the disulfide bonds. The activated oligonucleotides were then added to the amine-functionalized surface for covalent bonding.

Signalling oligonucleotides were immobilized on an ELISA plate as illustrated in FIG. 9. Briefly, bovine serum albumin (BSA, 5% w/v, Sigma) was adsorbed onto an ELISA plate (Thermo Scientific) as protein scaffold and activated by incubating with sulfosuccinimidyl 4-(N-maleimidomethyl)cyclohexane-1-carboxylate (sulfo-SMCC, 0.5 mg/ml, Pierce) for 30 min at room temperature. Plates were then washed with phosphate-buffered saline (Thermo Scientific) with 0.05% v/v Tween-20 (Sigma) (PBST). Separately, thiol-modified signalling oligonucleotides (Table 1, IDT) were activated by incubating with TCEP reducing gel (Pierce) to reduce the disulfide bonds for 1 h at room temperature. The reaction was then filtered and the gel washed several times to recover the activated oligonucleotides. The activated oligonucleotides were then added to the prepared BSA-coated plate and incubated for 2 h at room temperature. After washing with PBST, the plate was blocked with 2% BSA for 1 h at room temperature. The plate was then washed with PBST and the reaction buffer before sample application.

Amplification of Polymerase Activity by Horseradish Peroxidase (HRP).

Two forms of signalling oligonucleotides were used and evaluated to amplify and transduce different types of polymerase activity, namely exonuclease- and elongation-based activity. In both approaches, control wells containing no polymerase were run concurrently to provide the baseline signal. For the exonuclease-based strategy, we immobilized dumbbell DNA signalling structures on the plate and measured the polymerase activity (5' exonuclease activity) through the catalytic removal of biotin-modified nucleotides from the immobilized dumbbells. Briefly, we mixed sample targets with transition-state molecular switches and directly incubated the reaction with immobilized oligonucleotides, in the presence of dNTPs (Thermo Scientific), for 30 min at room temperature. Following washing steps with PBST and incubation with streptavidin-conjugated horseradish peroxidase (HRP, Thermo Scientific), we applied QuantaRed chemifluorescence substrate (Thermo Scientific) and measured the fluorescence intensity (Tecan) to evaluate the removal of biotin-modified nucleotides.

For the elongation-based strategy, polymerase activity was measured through the incorporation of biotin-modified nucleotides to self-priming, hairpin DNA signalling structures immobilized on the plate. Sample and molecular switches were added to the signalling structures and incubated in the presence of biotin-modified dNTPs mixture (TriLink BioTechnologies). Following incubation for 30 min at room temperature and washing with PBST, we incubated streptavidin-conjugated HRP (Thermo Scientific). After washing, we applied QuantaRed chemifluorescence substrate (Thermo Scientific) and measured the fluorescence intensity (Tecan) to evaluate the addition of biotin-modified nucleotides.

CATCH Assay (Plate Format).

Transition-state molecular switches were prepared as previously described. Sample containing target was mixed with the prepared molecular switches to a final volume of 50 μl. The mixture was added to the self-priming DNA signalling structures, immobilized on the plate, in the presence of biotin-modified dNTP mixture. The reaction mixture was incubated for 30 min at room temperature. Following washing steps with PBST and incubation with streptavidin-conjugated horseradish peroxidase (HRP, Thermo Scientific), we applied QuantaRed chemifluorescence substrate (Thermo Scientific) and measured the fluorescence intensity (Tecan). For each sample, sample-matched positive (containing polymerase without inhibitory complex) and negative (scrambled molecular switch) controls were run concurrently for data normalization.

Device Fabrication.

A prototype microfluidic device was fabricated through standard soft lithography as previously described [X. Wu, et al., *Sci Adv* 6, eaba2556 (2020)]. Briefly, 50-μm-thick cast molds were patterned with SU-8 photoresist and silicon wafers using a cleanroom mask aligner (SUSS MicroTec) and developed after ultraviolet (UV) exposure. Polydimethylsiloxane (PDMS, Dow Corning) and cross-linker were mixed at a ratio of 10:1 and casted on the SU-8 mold. The polymer was first cured at 75° C. for 30 min. Then, multiple nylon screws and hex nuts (RS Components) were positioned on the PDMS film over their respective channels and embedded in the PDMS, before a final curing step.

Device Preparation.

To immobilize the signalling oligonucleotides on the device, we treated the device's glass surface with (3-aminopropyl)triethoxysilane (APTES, 2% v/v, Sigma) in 95% ethanol for 1 h at room temperature. The chambers were then flushed with ethanol to remove excess APTES and dried. Separately, thiol-modified signalling oligonucleotides were activated as previously described. The activated oligonucleotides were then flowed in and incubated for 2 h at room temperature. After flushing with PBST to remove excess oligonucleotides, the chambers were blocked with 2% BSA for 1 h at room temperature. The chambers were then washed with PBST and the reaction buffer. To prepare the device for operation, we lyophilized the assay reagents within the device. The reagent mixture, containing inhibitor strand, enhancer strand, polymerase and biotin-modified dNTP mixture, was flowed into the device and lyophilized overnight (Labconco).

CATCH Assay (Microfluidic Chip Format).

Operation steps of the microfluidic device are illustrated in FIG. 4. In a typical assay, 5 μl of sample was introduced to each of the three inlets for measurement of sample, sample-matched positive and negative controls (paths 1, 2 and 3, respectively). Positive pressure was applied to flow the samples to the respective detection chambers. The solution was incubated within the device for 30 min at room temperature. After flushing with PBST, 5 μl streptavidin-conjugated HRP was introduced and incubated for 5 min at room temperature. The unbound streptavidin conjugates were then removed and 5 μl QuantaRed chemifluorescence substrate (Thermo Scientific) was added. The resultant fluorescence intensity was measured on the detection chambers (see FIG. 3) through a smartphone-based optical sensor.

Smartphone-Based Optical Sensor.

To enable smartphone analysis of the microfluidic CATCH assay, we developed a sensor that comprised a LED source, an optical filter and a magnification lens within a 3D-printed optical cage as previously described [X. Wu, et al., *Sci Adv* 6, eaba2556 (2020)]. The optical cage was fabricated from a UV-curable resin (HTM 140) using a desktop 3D printer (*Aureus*). The central wavelengths of the LED light source (Chaoziran S&T) and optical filter (Thorlabs) were 500 and 600 nm, respectively. The magnification lens (Thorlabs) was placed before the smartphone camera to improve the image quality. The assembled system measured 45 mm (width) by 45 mm (length) by 50 mm (height) in dimension and was equipped with two sliding slots for quick attachment to smartphones (Apple). Sensor performance was evaluated against a commercial microplate reader (Tecan) for different fluorescent dyes and intensities.

Data Normalization.

$$I_{norm}=(I_{target}-I_{control})/(I_{pol}-I_{control})$$

where $I_{norm}$ is the normalized fluorescence intensity, $I_{target}$ is the fluorescence intensity of the sample incubated with molecular switches against the target, $I_{control}$ is the fluorescence intensity of the sample-matched negative control, incubated with scrambled control molecular switches, and $I_{pol}$ is the fluorescence intensity of the sample-matched positive control, incubated with active polymerase.

Evaluation of CATCH Performance.

To evaluate the specificity of the transition state compared to that of the closed state, molecular switches were mixed with targets with varying number of mismatches at positions that would most drastically affect the signal produced by the molecular switches [Ho N R Y et al., *Nat Commun.* 2018, 9: 3238] (Table 1). The resultant polymerase activity was measured using the assay on the plate as previously described. To characterize the sensitivity of the assay, we prepared serial ten-fold dilutions of the target and mixed the target samples with molecular switches in distinct states (e.g., transition vs. closed states) to evaluate changes in polymerase activity. To investigate the incubation time required to recover the functionality of lyophilized switches, we reconstituted the lyophilized reagents with the reaction buffer and incubated the mixture for less than 1 min, 5 min, 10 min, and 30 min before mixing with target and transferring to the functionalized plate for signalling. To evaluate the performance of lyophilized switches, we mixed lyophilized and non-lyophilized switches with target and the resultant polymerase activity was measured through 5' exonuclease degradation of fluorescent signalling probe as previously described.

Cell Culture and Lysis.

Human lung epithelial cell line (PC9) was obtained from American Type Culture Collection (ATCC) and grown in RPMI-1640 medium (HyClone) supplemented with 10% fetal bovine serum (FBS, HyClone) and 1% penicillin-streptomycin (Gibco) in a humidified 37° C. incubator with 5% $CO_2$. The cell line was tested and free of mycoplasma contamination (MycoAlert Mycoplasma Detection Kit, Lonza, LT07-418). To evaluate the performance of the assay in biological samples, we prepared cell lysates through different protocols and spiked in synthetic target oligonucleotides, before testing the samples with molecular switches. RNase inhibitor was added to all lysate mixtures. Specifically, we lysed cell pellets through heating or incubating with detergent buffer. For heat treatment, cell pellets were resuspended in the reaction buffer and heated at 56° C. for 30 min, 70° C. for 5 min, or 90° C. for 5 min [Chin A W H, et al., *The Lancet Microbe.* 2020, 1: e10; Ladha A et al., *medRxiv* (2020). Doi.org/10.1101/2020.05.07.20055947]. For chemical lysis, we prepared lysis buffers, by mixing the reaction buffer with varying amounts of single or a mixture of detergents: Triton X-100, sodium dodecyl sulfate (SDS), Saponin, Tween-20, Igepal CA-630, NP-40 (Sigma). To optimize the chemical lysis composition and incubation duration, we evaluated various lysis conditions for their ability to rapidly lyse cells while maintaining good polymerase activity. To assess cell lysis efficiency, cells were incubated with the lysis buffers and the resultant cell numbers were counted using Countess II Automated Cell Counter (Thermo Scientific). Polymerase activity was measured through 5' exonuclease degradation of fluorescent signalling probe, as described above.

RNA Extraction and Detection.

RNA extraction was performed with a commercially available kit (RNeasy Mini, Qiagen) per manufacturer's protocol. Extracted RNA was quantified with Nanodrop spectrophotometer (Thermo Scientific). To detect specific RNA targets through gold-standard RT-qPCR analysis, extracted RNA was first reverse-transcribed to generate first-strand cDNA (MultiScribe Reverse Transcriptase, Thermo Scientific). For PCR analysis, to detect housekeeping genes (i.e., GAPDH and beta-actin), we used Taqman Fast Advanced Master Mix (Thermo Scientific) and primer sets (Taqman gene expression assays, Thermo Scientific) as recommended by the manufacturer. Amplification conditions consisted of 1 cycle of 95° C. for 2 min, 45 cycles of 95° C. for 1 s and 60° C. for 20 s. All thermal cycling was performed on a QuantStudio 5 real-time PCR system (Applied Biosystems).

Clinical Measurements

A total of 48 clinical samples consisting of extracted RNA and heat-inactivated swabs were evaluated in this study. To determine the diagnostic performance of the CATCH assay, extracted RNA samples (positive, n=20; negative, n=9) were used directly on the CATCH assay, while swab lysates (positive, n=9; negative, n=10) were prepared through heating at 70° C. for 30 min, before measurement by the CATCH assay. SARS-CoV-2 clinical diagnoses were generated by commercial RT-qPCR assay (Fortitude Kit, MiRXES). Amplification conditions consisted of 1 cycle of 48° C. for 15 min, 1 cycle of 95° C. for 150 s, 42 cycles of 95° C. for 10 s and 59° C. for 42 s. $C_t$ value <40 was determined as positive as per CDC's guidelines [Centers for Disease Control and Prevention, CDC 2019-Novel Coronavirus (2019-nCoV) Real-Time RT-PCR Diagnostic Panel. (2020), available at worldwidewebdotfda.gov/media/134922/download]. All measurements on clinical samples were performed in an anonymized and blinded fashion and finalized before comparison with clinical $C_t$ value.

Statistical Analyses

Unless otherwise stated, all measurements were performed in biological triplicate, and the data are presented as mean±standard deviation. For inter-sample comparisons, multiple pairs of samples were each tested via Student's t-test, and the resulting P values were adjusted for multiple hypothesis testing using Bonferroni correction. An adjusted $P<0.05$ was determined as significant. Receiver operating characteristic (ROC) curves were generated from patient profiling data and constructed by plotting sensitivity versus (1—specificity), and the values of area under the curve (AUC) were computed using the trapezoidal rule. The clinical reports were used as classifiers (true positives and true negatives). Detection sensitivity, specificity and accuracy were calculated using standard formulas. Statistical analyses were performed using GraphPad Prism software (version 7.0c).

Example 2

CATCH Platform

Figure 1:
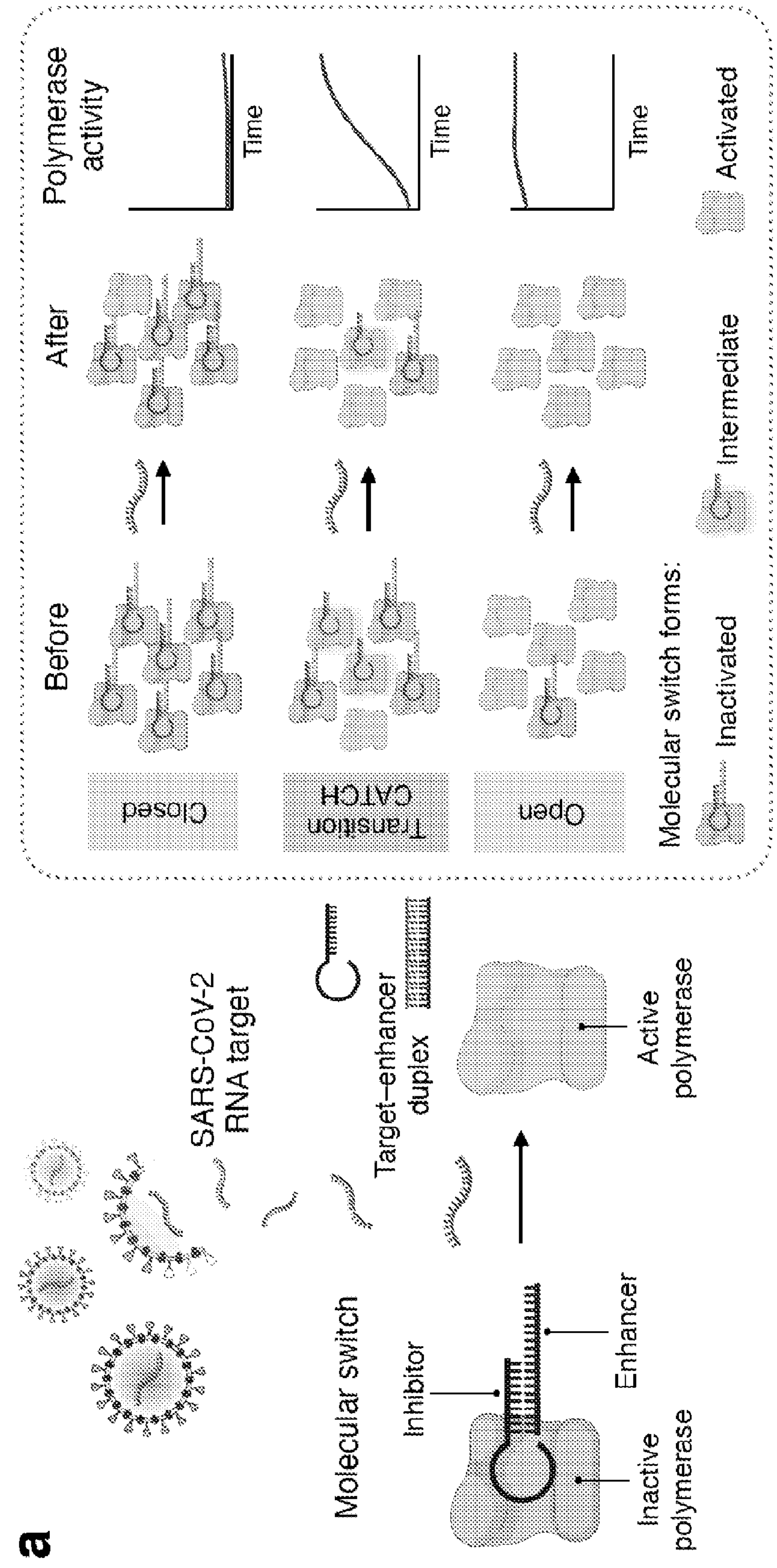
FIG. 1 shows catalytic amplification by transition-state molecular switch (CATCH). (a) Schematic representation of the CATCH assay. The CATCH assay leverages the specific binding of nucleic acid targets (SARS-CoV-2 viral RNA) to activate molecular switches. Each molecular switch consists of a Taq DNA polymerase and an inhibitory DNA complex, comprising an inhibitor strand and an enhancer strand that binds and inactivates the polymerase. As the viral RNA target hybridizes with the enhancer strand, it destabilizes the inhibitory complex and releases the active polymerase (left). By adjusting the ratio of molecular constituents in individual switches, we prepare molecular switches in different states of target-responsiveness: closed, transition and open (right). In the closed state, switches are fully inactivated, due to excess inhibitory complexes, and cannot be readily activated by sparse RNA targets. In the open state, switches are fully activated and largely unresponsive to targets due to a high initial background. In the transition state, different forms of switches exist in a delicate equilibrium, that a small amount of RNA targets can readily shift this equilibrium to favor the formation of more activated switches. The transition-state switches thus demonstrate maximal responsiveness (i.e., the largest change in polymerase activity within the shortest timespan). (b) Signal generation. To enhance the detection signal, the CATCH assay recruits additional enzymatic cascades to transduce and amplify the target-induced polymerase activity as a fluorescence readout (see FIG. 8*a* for more details). As compared to that using the closed- or open-state molecular switches, the CATCH assay (transition state) generates strong signals from clinical samples with a low viral load. (c) Different assay formats. The CATCH assay can be performed in a 96-well format for high-throughput applications (top) or a miniaturized microfluidic device for portable, smartphone-based detection (bottom).
Figure 1:
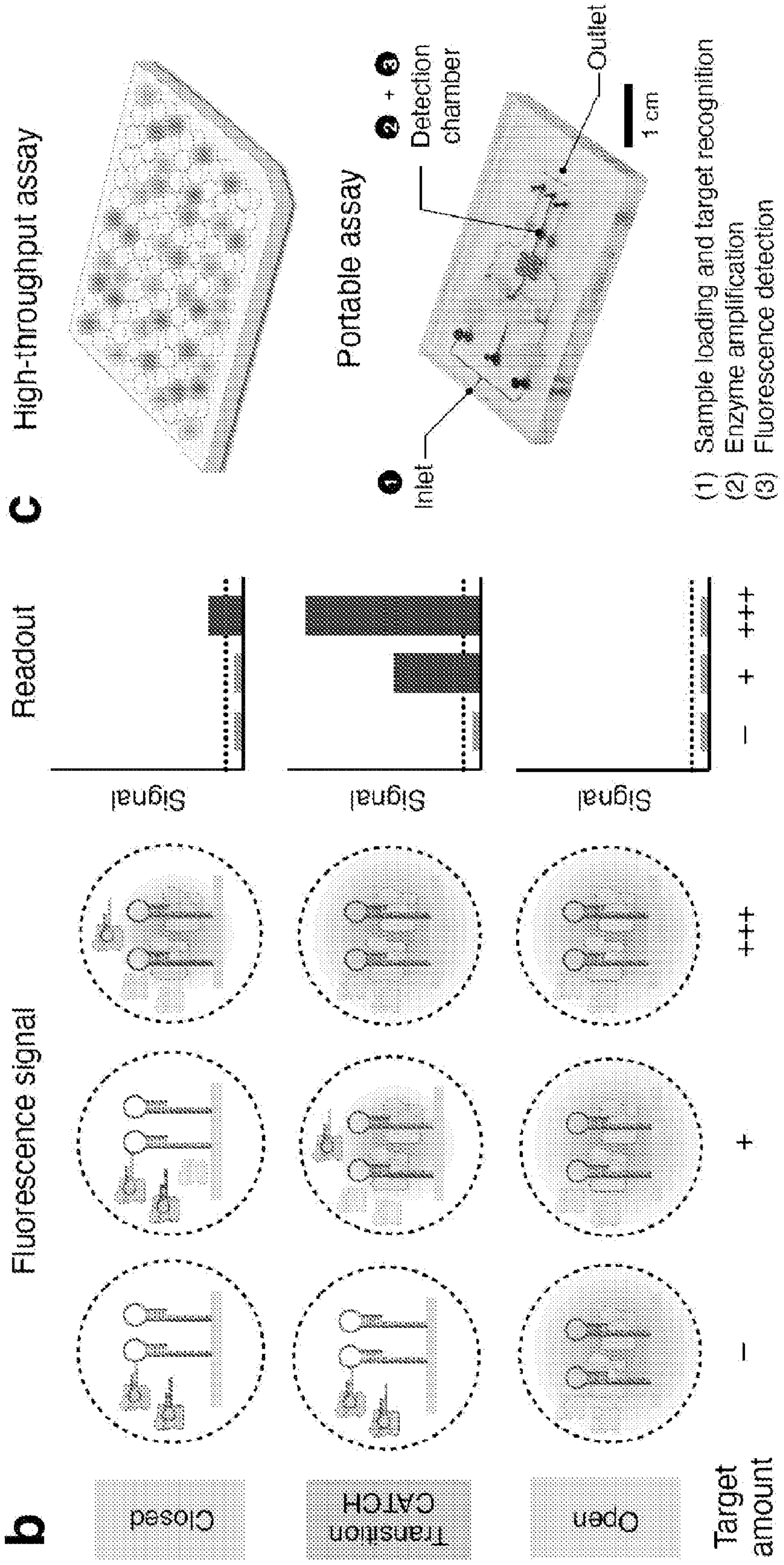

The working principle of the CATCH assay is illustrated in FIG. 1*a*. Clinical samples containing SARS-CoV-2 viral RNA targets are mixed with a DNA-enzyme molecular switch for direct and sensitive detection. The hybrid switch consists of an inhibitory DNA complex—comprising an inhibitor strand and an enhancer strand—that binds and inactivates Taq DNA polymerase [Dang C et al., *J Mol Biol.* 1996, 264: 268-278]. We design the inhibitory DNA complex to be complementary to various SARS-CoV-2 RNA targets (FIG. 6*a*); only in the presence of specific target RNA, the enhancer hybridizes with the target and the inhibitor is displaced, thereby releasing and activating the polymerase. The inhibitor strand is a stem-loop structure which consists of a conserved region (loop) and a variable region (stem). Interestingly, we found that while the inhibitor strand alone can weakly decrease the polymerase activity, simultaneous addition of the enhancer strand strongly inhibits the polymerase activity (FIG. 6*b*). This is likely due to the improved stabilization of the stem-loop conformation as a result of the hybridization of the enhancer strand to the stem of the inhibitor strand, resulting in an enhancement of its inhibitory effect [Dang C et al., *J Mol Biol.* 1996, 264: 268-278; Hasegawa H et al., *Molecules.* 2016, 21; 421]. Motivated by the strong toggling effect by the enhancer strand and the multi-component dynamic equilibrium (i.e., intra-switch and inter-switch), we reason that by adjusting the ratio of molecular constituents of individual switches, we can tune the molecular switches to achieve different states of target-responsiveness: closed, transition and open (FIG. 1*a*, right). In the closed state, most of the molecular switches are fully inactivated, through polymerase binding with excess inhibitory complexes; turning on the polymerase activity thus requires a large amount of RNA targets. In the open state, most of the molecular switches are fully activated; turning on additional polymerase activity amidst a high initial background results in a low net signal. In the transition state, different forms of molecular switches (i.e., inactivated, intermediate and activated) (FIG. 6*c*) exist in a delicate dynamic equilibrium; a small amount of target molecules can readily shift the equilibrium to favor the formation of more activated switches, thereby triggering a large increase in overall polymerase activity.

Figure 3:
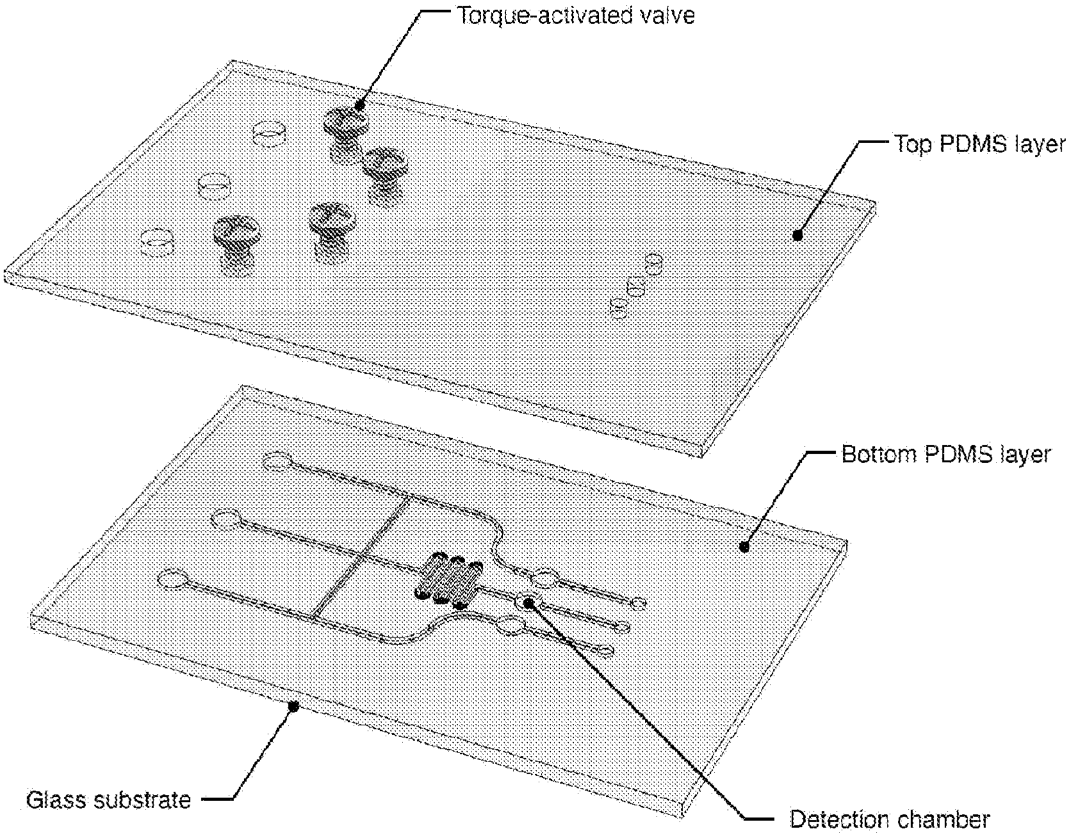
FIG. 3 shows an exploded view of the microfluidic device. The platform was assembled from two polydimethylsiloxane (PDMS) layers on a glass substrate, with torque-activated valves for sequential flow control.
Figure 5:
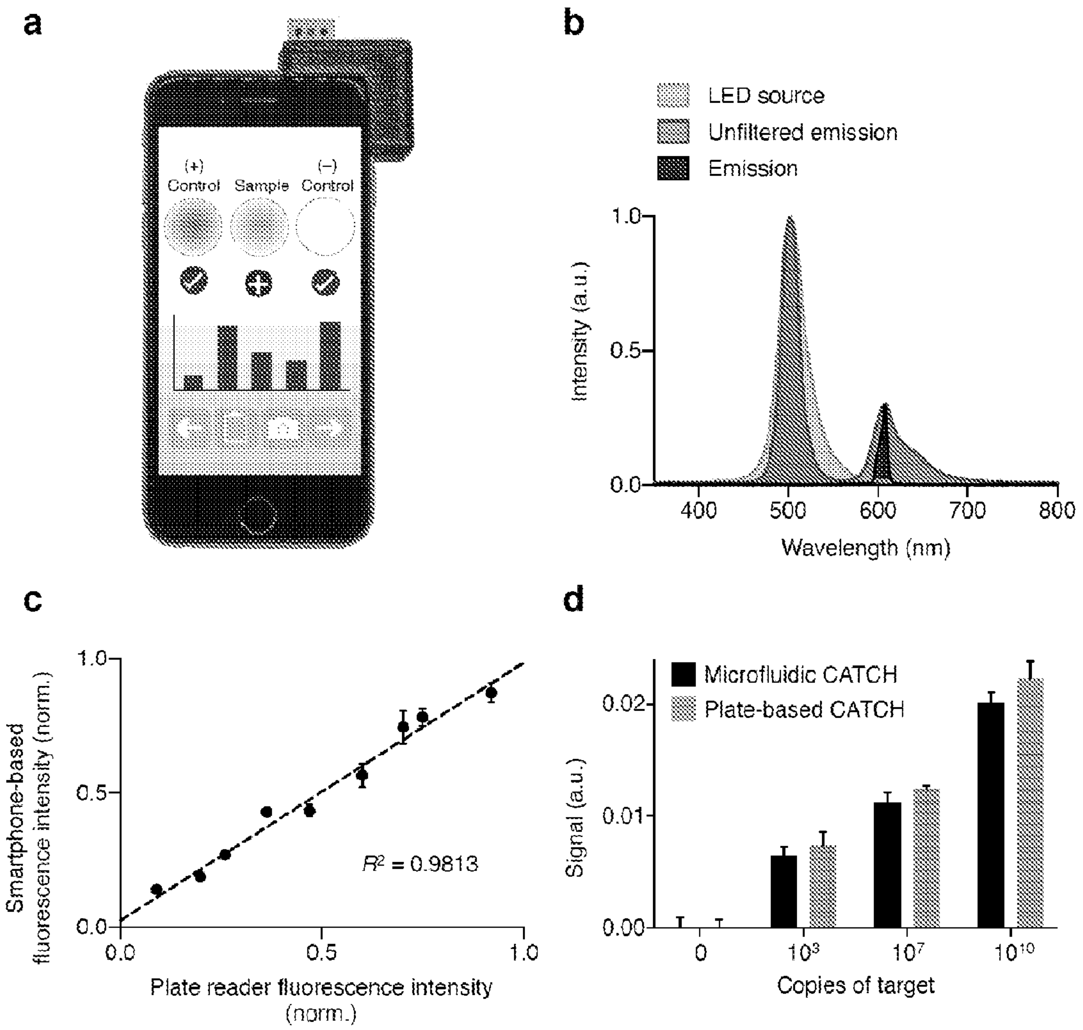
FIG. 5 shows a portable CATCH assay. (a) Photograph of the smartphone-based fluorescence detector. (b) Optical spectra of the LED source, unfiltered and filtered fluorescence emission. (c) Correlation of the smartphone-based detector and conventional plate reader. The smartphone-based detector correlates well with the commercial reader ($R2=0.9813$). (d) CATCH assay performance in microfluidic and plate format. The CATCH assay in its microfluidic chip format demonstrated good consistency with the assay in its plate format. All measurements were performed in triplicate, and the data are presented as mean±s.d. in c and d. a.u., arbitrary unit.

By ratiometric tuning of various switch components, we found the transition-state switches to be hyper-responsive to RNA targets, and leveraged this state to develop the CATCH assay for rapid, sensitive detection of SARS-CoV-2. To further enhance the detection signal, we measured the changes in polymerase activity through additional enzymatic amplification (FIG. 1*b*). Specifically, we utilized the target-induced polymerase activity to incorporate biotin-modified deoxynucleotide triphosphates (biotin-dNTPs) into immobilized hairpin oligonucleotides and this incorporation to recruit streptavidin-conjugated enzymes (horseradish peroxidase) for the development of chemifluorescence signal. As compared to assays using the closed- or open-state molecular switches, the CATCH assay (transition state) generates strong signals from mildly positive patients with a low viral load. Importantly, the CATCH assay could be versatilely implemented to accommodate different diagnostic needs (FIG. 1*c*). For example, the signalling oligonucleotides can be immobilized onto a 96-well plate for high-throughput applications; this assay configuration closely resembles conventional ELISA in terms of assay workflow and readout, enabling its easy adaptation in clinical laboratories with standard instrumentation. The CATCH assay can also be implemented on a miniaturized microfluidic device (FIGS. 3 and 4). Furthermore, chemifluorescence signals can be readily detected through a portable, smartphone-based fluorescence detector with comparable performance (FIG. 5).

Example 3

Transition-State Molecular Switches

To develop the CATCH assay for detecting SARS-CoV-2, we designed molecular switches as specific probes against the viral RNA. We chose regions of the spike (S) gene [Yan C et al., *Clin Microbiol Infect.* 2020, 26: 773-779] and the nucleocapsid (N) gene [Broughton J P et al., *Nat Biotechnol.* 2020, 38: 870-874] of the virus as specific targets and constructed distinct molecular switches based on these sequences (FIG. 6*a* and Table 1). To identify the transition state of the molecular switches, we first evaluated the effect of the inhibitory complex on Taq polymerase. Specifically, to a fixed concentration of polymerase, we titrated an increasing concentration of the inhibitory complex (i.e., varying the complex concentration but keeping the ratio of enhancer:inhibitor to 1:1). We observed that polymerase activity was markedly inhibited when incubated with >20 nM of inhibitory complex (FIG. 6*b*). Plotting the first derivative of the inhibition curve, we categorized the molecular switches in three groups, namely open, responsive, and closed (FIG. 6*b*, inset and FIG. 7*a*). Open-state molecular switches were made with a low concentration of inhibitory complex (<20 nM). In the responsive range, switches were prepared with a moderate concentration of inhibitory complex and remained responsive to changes in the inhibitory complex concentration (i.e., at the vertex, where switches were the most responsive, switches were made with 36 nM of inhibitory complex). Closed-state molecular switches were made with a high concentration of inhibitory complex (>60 nM). Importantly, when we perturbed the system through a reduction in the amount of enhancer strand (i.e., reducing the ratio of enhancer:inhibitor), molecular switches in the responsive state demonstrated large changes in their polymerase activity (FIG. 7*b*).

To establish the transition state, we further tuned the responsive-state molecular switches by titrating the amount of enhancer strand (i.e., through which target hybridizes and activates the switch) while keeping constant the amount of inhibitor strand (FIG. 6*c*). Through this optimization, we defined the transition state as the vertex on the first derivative inhibition plot (FIG. 6*c*, inset). This identified transition state demonstrated further improvement in its responsiveness, producing the largest increase in polymerase activity, while the open- and closed-state switches failed to produce any distinguishable signal (FIG. 7*c*). We further evaluated the performance of the transition-state molecular switches. The ratiometric-tuned switches not only demonstrated significant polymerase activity upon incubating with complementary on-target RNA sequences, but also maintained a low background activity when treated with off-target sequences (FIG. 6*d*). More importantly, for both the S-gene (FIG. 6*e*) and N-gene molecular switches (FIG. 7*d*), the transition-state switches achieved much faster activation kinetics. As compared to switches prepared in the other states, the transition-state switches enabled rapid polymerase activation. Different target concentrations could be distinguished within 30 minutes of incubation at room temperature (FIG. 7*e*).

Example 4

Signal Generation and Amplification

Figure 8:
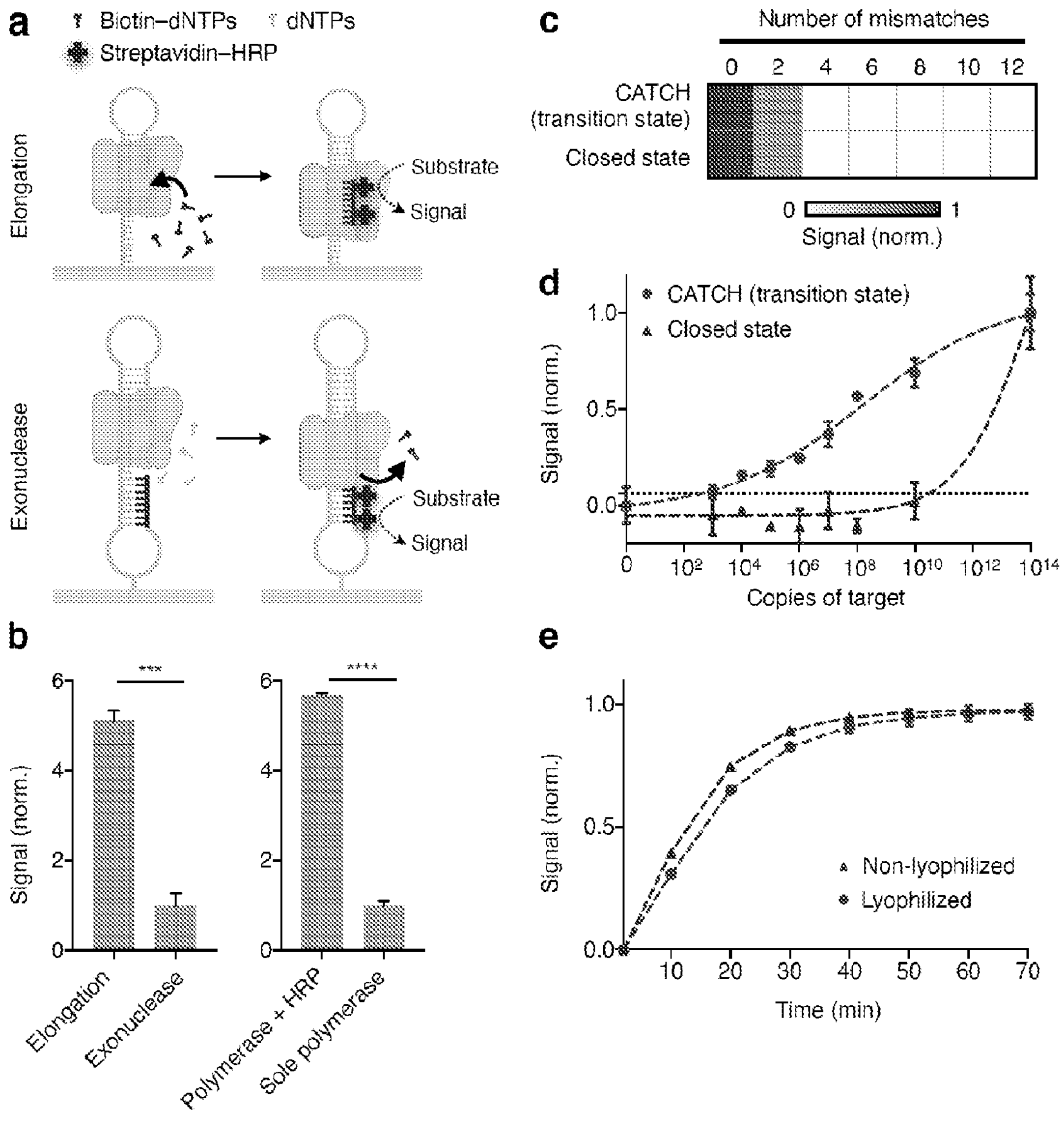
FIG. 8 shows signal enhancement through multi-enzyme cascades. (a) Schematic of two signalling oligonucleotide structures for the measurement of elongation and exonuclease activity of polymerase, respectively. In the elongation-based strategy, active polymerase incorporates biotin-modified dNTPs to the growing 3'-ends of self-primed hairpin oligonucleotides. After the addition of streptavidin-conjugated horseradish peroxidase (HRP) and substrate, fluorescence signal can be read out. In the exonuclease-based strategy, active polymerase cleaves biotin-modified nucleotides upon reaching the self-hybridized 5'-ends, thereby reducing the amount of HRP incorporation as well as the resultant fluorescence signal. (b) Elongation-based signal enhancement. When treated with an equal amount of polymerase, the elongation-based strategy showed a higher signal as compared to that by the exonuclease-based strategy (left). The recruitment of an additional enzymatic cascade (HRP) enhanced the signal significantly as compared to measurements based with sole polymerase activity (right). (c) Specificity of the CATCH assay. The CATCH assay, which utilizes transition-state molecular switches, showed uncompromised specificity against target mismatches, as compared to that by the closed-state molecular switches. (d) Sensitivity of the CATCH assay. The detection limits (dotted lines) were defined as 3× s.d. of the no-target controls and determined by titrating known quantities of target in a total volume of 50 μl and measuring their corresponding fluorescence signal. (e) Lyophilization of the CATCH assay. Assay reagents (molecular switches and biotin-dNTPs) were lyophilized to facilitate portable applications. The lyophilization preserved the switch performance. All measurements were performed in triplicate, and the data are presented as mean±s.d. in (b), (d), and (e) and as mean in (c). (**$P<0.0001$, *$P<0.005$, Student's t-test).
Figure 10:
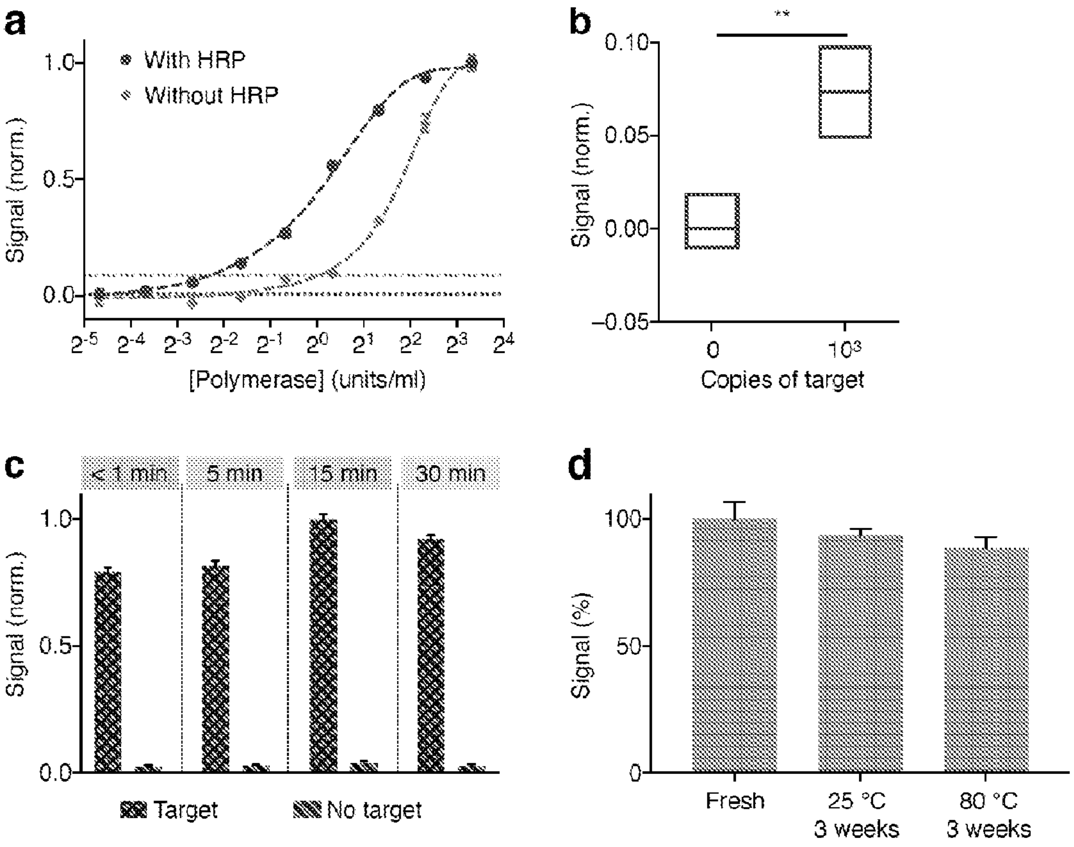
FIG. 10 shows CATCH signal amplification and portable integration. (a) Improved performance through additional enzyme recruitment. Through the recruitment of an additional enzyme cascade (horseradish peroxidase, HRP), the CATCH assay generated fluorescence signals even at a low amount of polymerase activity. (b) CATCH performance with a low amount of target. Significant signal difference was observed between no-target control and 1,000 copies of target. (c) Lyophilization of molecular switch reagents. To facilitate portable applications, we lyophilized the CATCH reagents (i.e., molecular switch and biotin-modified dNTPs). The lyophilized reagents were then reconstituted for <1 min, 5 min, 10 min, and 30 min, before being mixed with target oligonucleotides. The lyophilized molecular switches demonstrated spontaneous assembly and preserved functionalities. (d) Accelerated aging of lyophilized molecular switches. Reagents were lyophilized and their activity measured after 3 weeks at room temperature (25° C.) and under accelerated aging (80° C.). All measurements were performed in triplicate, and the data are presented as mean±s.d. (**P<0.01, Student's t-test).

Next, we devised a signalling mechanism to enzymatically amplify and measure the switch-induced polymerase activity. Specifically, we designed two signalling oligonucleotide structures to leverage different types of polymerase activity (i.e., elongation vs. exonuclease activity) and recruit additional enzymatic cascades (i.e., horseradish peroxidase, HRP) for signal amplification (FIG. 8*a*). We immobilized the oligonucleotide structures on a 96-well ELISA plate through protein scaffold (FIG. 9). In the elongation-based strategy, the active polymerase incorporates biotin-modified dNTPs to the growing chains of the self-primed hairpin oligonucleotides (3'-end). Fluorescence signal is then generated after the addition of streptavidin-conjugated HRP and chemifluorescence substrate. In the exonuclease-based strategy, we constructed a dumbbell-shaped signalling oligonucleotide with biotin modifications at its 5'-end. Active polymerase extends the 3'-end of the oligonucleotide and, upon reaching the self-hybridized 5'-end, cleaves the biotin-modified nucleotides; when reacted with streptavidin-conjugated HRP, this removal of biotin groups reduces the amount of fluorescence signal. We evaluated the two strategies by treating both oligonucleotide structures with an equal amount of active polymerase, and measured the resultant changes in fluorescence signals. The elongation-based strategy showed a significantly higher signal as compared with the exonuclease-based strategy (FIG. 8*b*, left). We thus incorporated the elongation approach for CATCH signalling. In comparison to measurements based on sole polymerase activity, the additional HRP recruitment significantly enhanced the signal output (FIG. 8*b*, right) and expanded the detection dynamic range (FIG. 10*a*).

Motivated by the signalling performance, we developed the CATCH assay workflow to utilize transition-state molecular switches for responsive target recognition, and elongation-based multi-enzyme cascade for signal enhancement. Specifically, we mixed RNA targets with transition-state switches and directly incubated the reaction with immobilized oligonucleotides (30 minutes at room temperature) for signal transduction and enhancement. As compared to a similar assay using closed-state molecular switches (i.e., fully inactivated molecular switches and HRP-based signal enhancement), the CATCH assay demonstrated comparable specificity against target mismatches, even when the mismatches were introduced against the most sensitive segment of the switches (FIG. 8*c* and Table 1). More importantly, the transition-state switches showed superior performance. In a titration experiment, where target samples were serially diluted and incubated with different-state molecular switches, the CATCH assay achieved >107-fold improvement in its limit of detection (LOD of ~8 copies of target per μl) as compared to the closed-state molecular switches (FIG. 8*d* and FIG. 10*b*). To facilitate portable clinical application, we lyophilized the assay reagents (i.e., molecular switches and biotin-dNTPs) within the microfluidic device. The lyophilization not only preserved the assay performance, but also conferred excellent long-term stability (FIG. 8*e* and FIG. 10*c-d*).

Example 5

Assessment of CATCH Assay in Cellular Lysates

Figure 11:
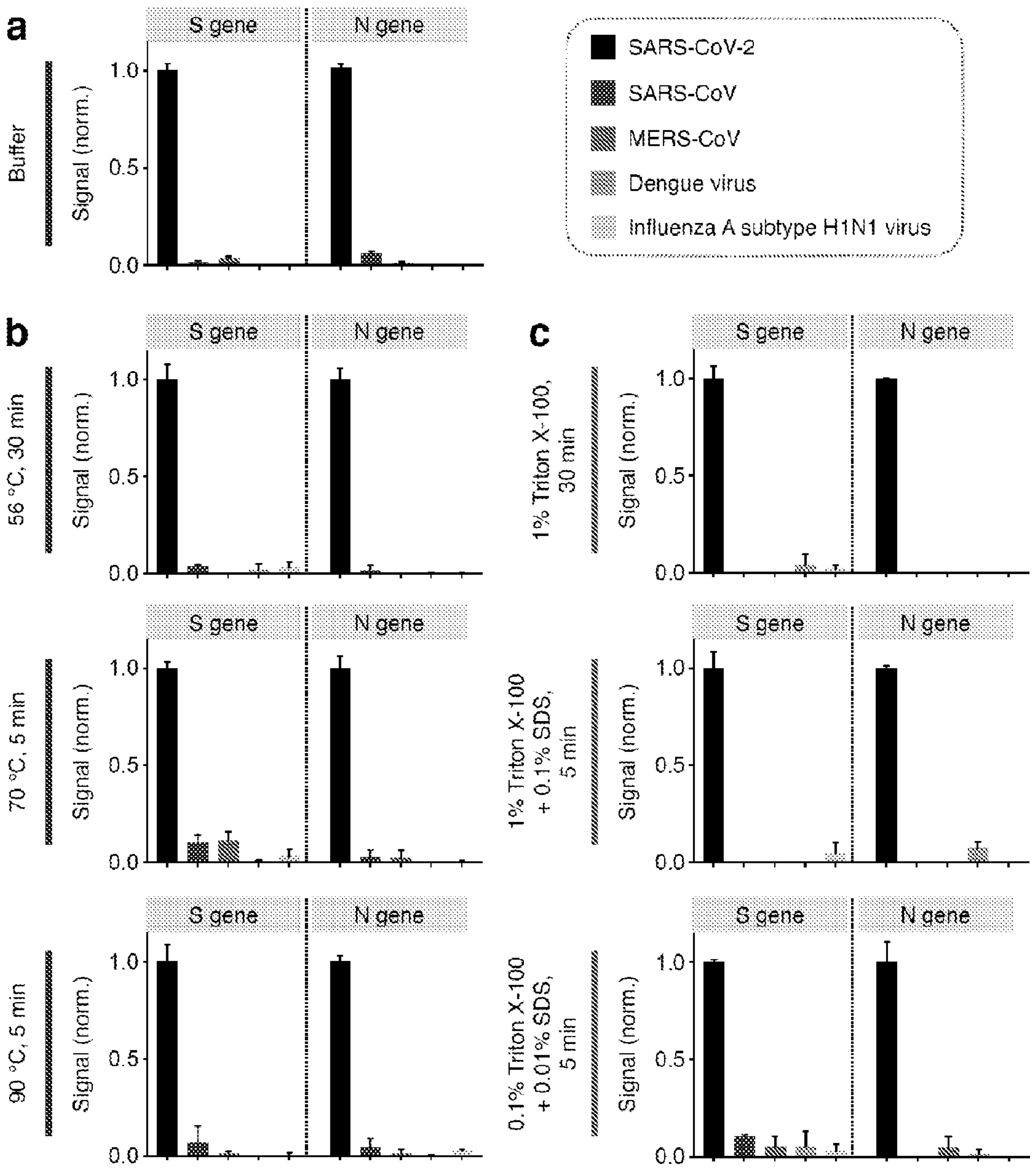
FIG. 11 shows specificity of CATCH in detecting SARS-CoV-2 in cellular lysates. Specificity of the CATCH assay in detecting S and N gene targets of SARS-CoV-2. Assay specificity was evaluated against sequences of other closely-related human coronaviruses (SARS-CoV and MERS-CoV) and other viruses causing diseases with similar symptoms (dengue virus and influenza A subtype H1N1 virus). Synthetic targets were spiked in (a) pure buffer or (b-c) cell lysates. Lysates were prepared through (b) thermal incubation at different temperature and duration or (c) chemical lysis using different combinations of detergents. The molecular switches maintained specific detection for SARS-CoV-2 targets and showed minimal cross-reactivity with off-target viral sequences, across all lysis conditions. All measurements were performed in triplicate and the data are presented as mean±s.d.

To address the need for extensive sample preparation in conventional qPCR (i.e., RNA extraction), we next determined if the CATCH assay could be developed to bypass this crucial and limiting step. Using specific molecular switches designed for SARS-CoV-2 RNA targets (i.e., S-gene and N-gene switches), which demonstrated specific detection and minimal activity against sequences of other closely-related human coronaviruses (SARS-CoV and MERS-CoV) as well as other viruses causing diseases with similar symptoms (dengue virus and influenza A subtype H1N1 virus) (FIG. 11*a*), we evaluated the performance of the CATCH assay in different cellular lysates.

Figure 12:
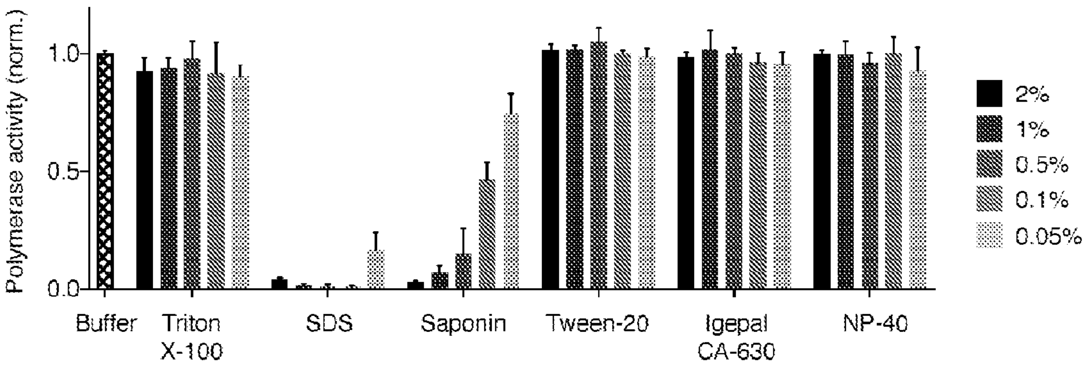
FIG. 12 shows the effects of detergents on polymerase activity. Polymerase activity was evaluated in the presence of various concentrations of single detergents. Polymerase activity was highly inhibited in the presence of sodium dodecyl sulfate (SDS) and gradually inhibited with increasing concentration of saponin. The other detergents tested showed negligible effects on polymerase activity, regardless of their applied concentrations. All measurements were performed in triplicate and the data are presented as mean±s.d.
Figure 13:
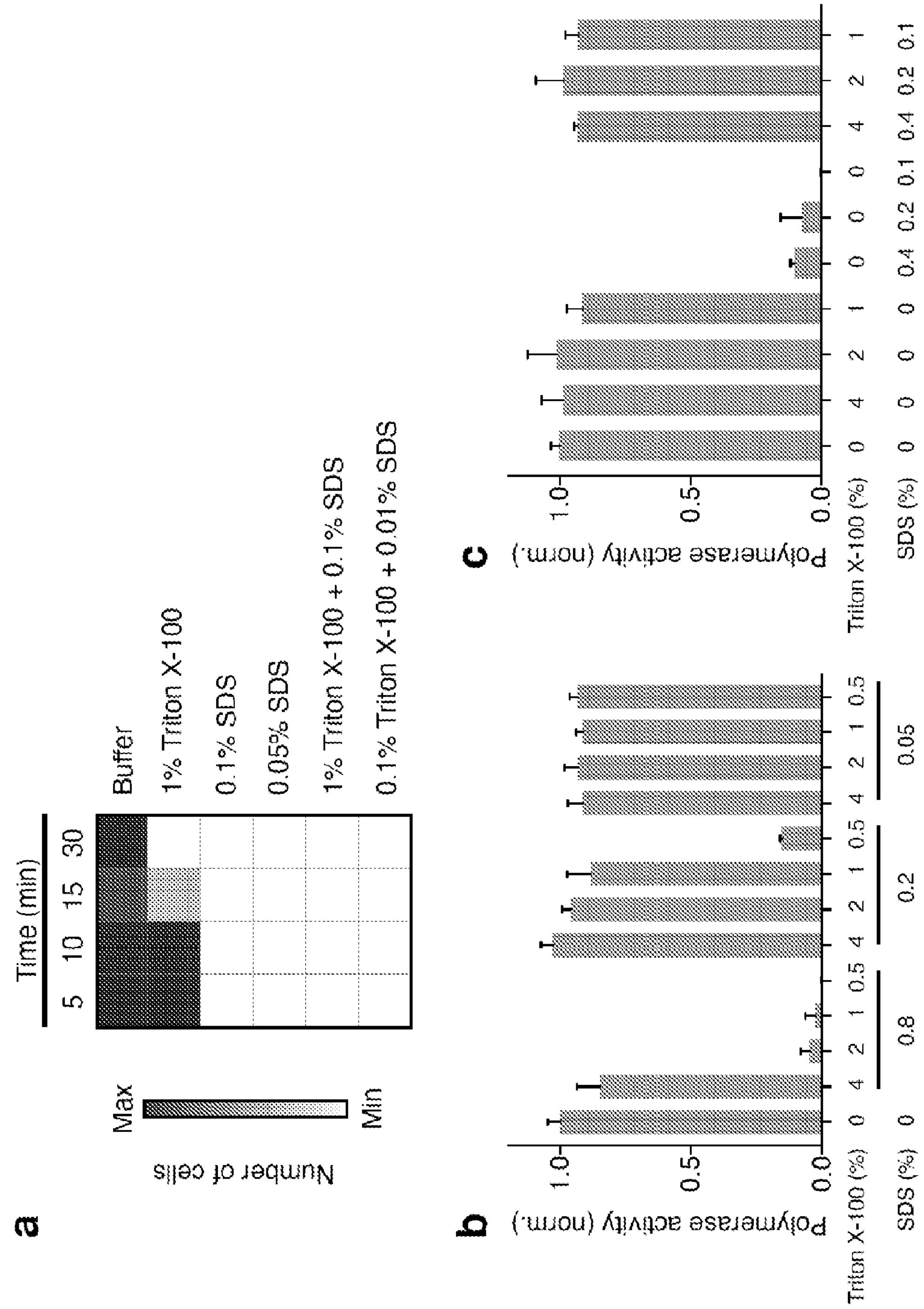
FIG. 13 shows the effects of detergents on ell lysing efficiency. (a) Single or a mixture of detergents were used to lyse cells. All detergents, except 1% Triton X-100, could efficiently lyse cells within 5 minutes. (b-c) Polymerase activity was evaluated in the presence of various combinations of Triton X-100 and SDS. An optimal ratio of 1:10 between SDS and Triton X-100 could both preserve polymerase activity and lyse cells within 5 minutes. All measurements were performed in triplicate and the data are presented as mean in (a) and as mean±s.d. in (b) and (c).

Specifically, we explored two modes of direct lysis, namely thermal (FIG. 11*b*) and chemical lysis (FIG. 11*c*), and used the lysates for direct CATCH detection. For thermal lysis, we investigated the effects of different temperature and heating duration on the lysis efficiency; three different temperature conditions, 56° C. for 30 min, 70° C. for 5 min, and 90° C. for 5 min, were selected based on published studies [Chin A W H, et al., *The Lancet Microbe.* 2020, 1: e10; Ladha A et al., *medRxiv* (2020) Doi.org/10.1101/2020.05.07.20055947]. For chemical lysis, to optimize the treatment conditions, we first evaluated polymerase activity in the presence of single detergents (FIG. 12). Polymerase activity was found to be highly inhibited in the presence of sodium dodecyl sulfate (SDS) and gradually inhibited with increasing concentration of saponin. Other tested detergents (e.g., Triton X-100) showed negligible effects on the polymerase activity. Using this information, we next optimized detergent combinations for rapid cell lysis (FIG. 13*a*) while maintaining good polymerase activity (FIG. 13*b*). We determined that an optimal ratio of 1:10 between SDS and Triton X-100 could both preserve polymerase activity and lyse cells within 5 minutes.

Figure 14:
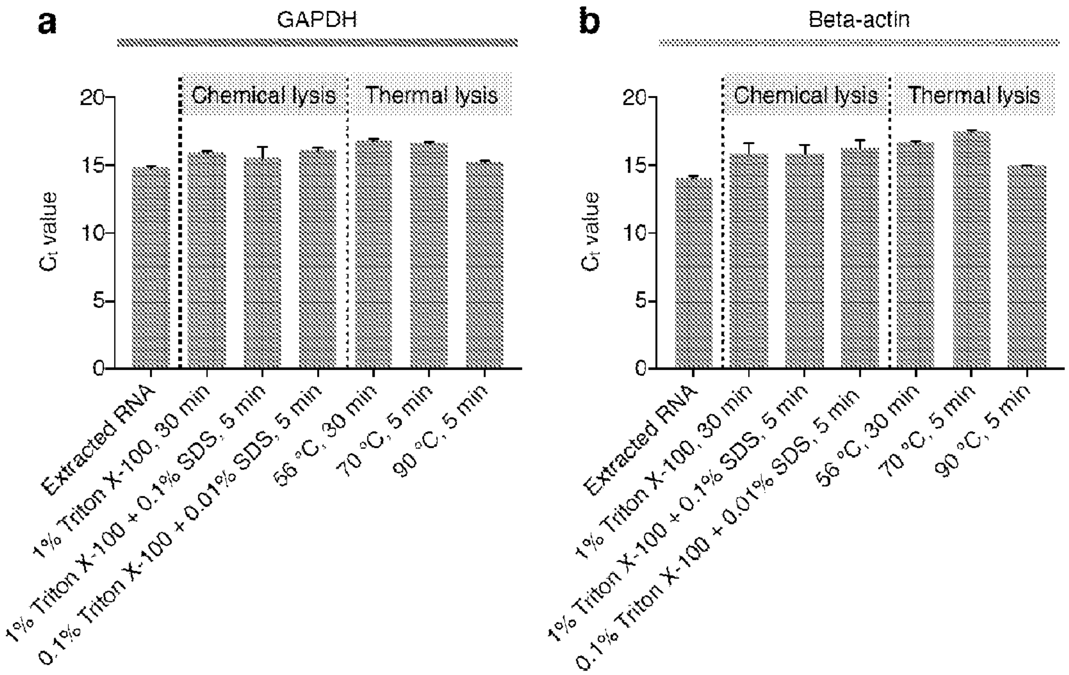
FIG. 14 shows release and preservation of endogenous RNA targets by chemical and thermal lysis. Endogenous mRNA targets GAPDH (a) and beta-actin (b) were measured in human lung epithelial cells. Gold-standard RNA samples were prepared from the cell culture through standard extraction. Chemical and thermal lysates were prepared respectively from an equivalent cell culture, without RNA extraction. All measurements were performed in triplicate, through RT-qPCR analysis. The lysis methods could effectively release and preserve endogenous RNA targets. The data are presented as mean±s.d.

With these selected thermal and chemical lysis protocols, we first validated the ability of these methods to release and preserve endogenous RNA targets (i.e., GAPDH and beta-actin) in human lung epithelial cells. We demonstrated that for both endogenous targets tested, when assayed via RT-qPCR, all lysates generated similar cycle threshold (Ct) values as compared with the gold-standard extracted RNA samples (FIG. 14). We further evaluated the compatibility of the lysis protocols with the developed CATCH assay. Using synthetic targets spiked into thermal lysates (FIG. 11*b*) and chemical lysates (FIG. 11*c*), we incubated the lysate mixtures with molecular switches for CATCH detection. Across all lysis conditions, the CATCH assay not only maintained strong and specific detection for SARS-CoV-2, but also showed minimal cross-reactivity with off-target viruses.

Example 6

SARS-CoV-2 Detection in Clinical Swab Samples

To test the clinical utility of the CATCH platform for SARS-CoV-2 detection, we conducted a feasibility study with patient samples. We aimed at addressing the following questions: (1) if the CATCH assay can be applied directly to detect extracted RNA of nasopharyngeal swab samples (i.e., bypassing RT-qPCR), (2) if the CATCH platform can be used for direct detection of swab lysates (i.e., bypassing RNA extraction), and (3) the accuracy of CATCH in COVID-19 diagnosis.

Figure 15:
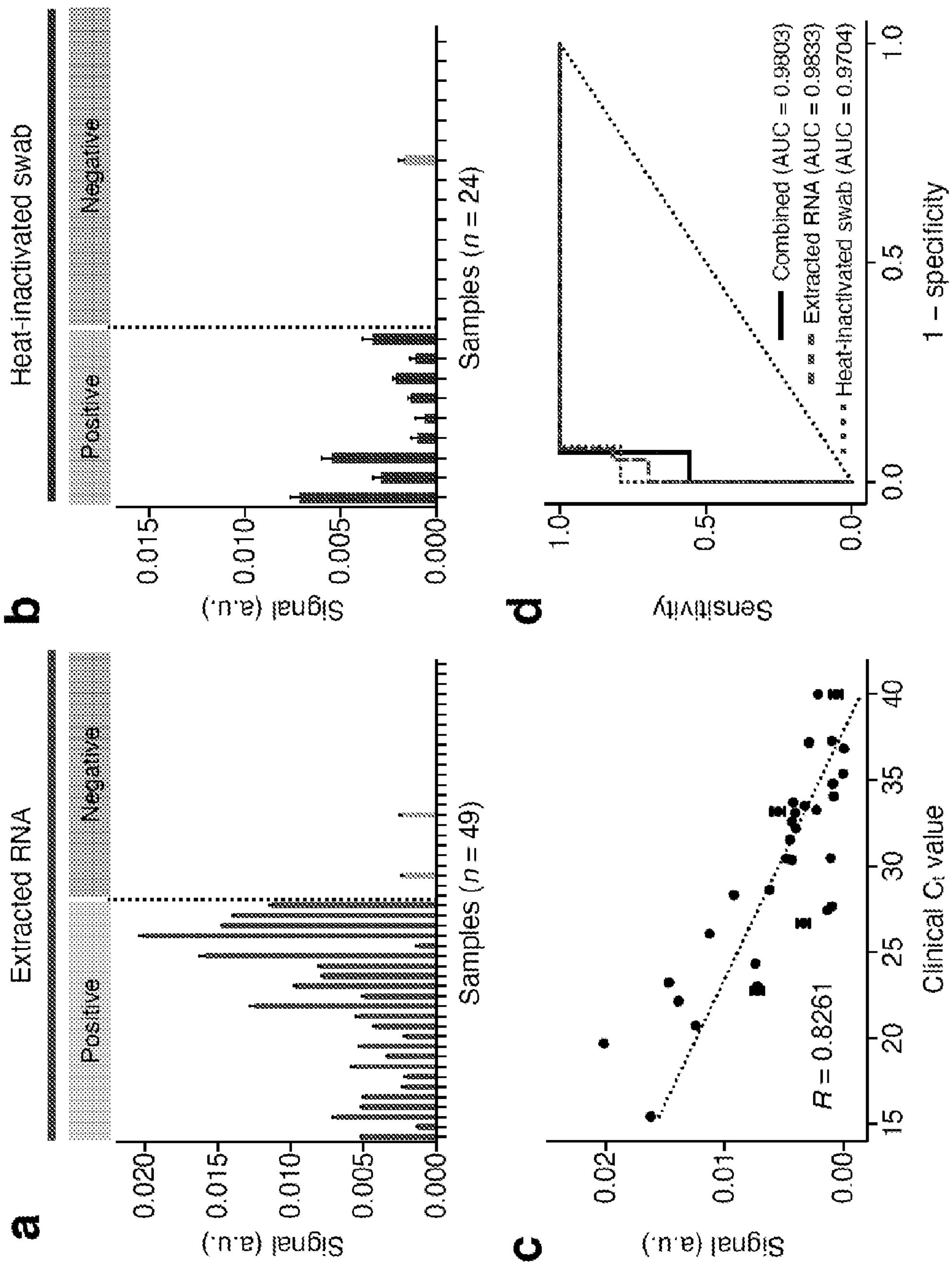
FIG. 15 shows clinical validation of CATCH for COVID-19 diagnosis. The CATCH assay was performed on (a) extracted RNA of nasopharyngeal swab samples (positive, n=24; negative, n=25) and (b) heat-inactivated swab lysates (positive, n=9; negative, n=15). (c) Correlation of CATCH assay with clinical RT-qPCR $C_t$ values. The CATCH assay demonstrated a good agreement with the clinical results (R=0.8261). (d) Receiver operator characteristic (ROC) curves of the CATCH platform. The CATCH analysis showed a high accuracy for SARS-CoV-2 detection (AUC=0.9803 for combined samples; AUC=0.9833 for extracted patient RNA; AUC=0.9704 for heat-inactivated swab samples). All measurements were performed in triplicate and the data are presented as mean±s.d in (a-c). a.u., arbitrary unit. AUC, area under curve.

We first tested swab-extracted RNA samples (n=49) using the CATCH assay. RNA samples were extracted through commercial columns and incubated directly with the CATCH mixture for 30 minutes at room temperature. Of the 49 extracted RNA samples, 24 were determined by gold-standard RT-qPCR assay as positive for COVID-19 infection and 25 as negative. The positive and negative diagnostic prediction of CATCH relative to the clinical RT-qPCR outcome were 100% and 92%, respectively (FIG. 15*a*). We further tested our assay in heat-treated swab samples (n=24), thereby omitting the RNA extraction steps. Of the 24 patient swab samples obtained, 9 were positive for COVID-19 infection, as determined by RT-qPCR assay, and 15 were negative for COVID-19 infection. The CATCH assay correctly identified 9 out of 9 (100%) positive samples and 14 out of 15 (93.34%) negative samples (FIG. 15*b*).

To evaluate the clinical performance, across all tested clinical samples, we correlated the CATCH assay with the matched RT-qPCR $C_t$ values (FIG. 15*c*). The CATCH assay demonstrated a good agreement with the clinical results (R=0.8261), and could sensitively detect samples with a low viral load ($C_t$>35). Compared with the RT-qPCR-based clinical diagnoses, the CATCH platform demonstrated a high accuracy for SARS-CoV-2 detection (FIG. 15*d*, area under the curve (AUC)=0.9803 for combined samples; AUC=0.9833 for extracted patient RNA; AUC=0.9704 for heat-inactivated swab samples). CATCH's ability to diagnose COVID-19 without the need for RNA extraction and RT-qPCR could thus facilitate faster, simpler, and cheaper diagnostic tests.

SUMMARY

Amongst current COVID-19 testing protocols, nucleic acid detection, particularly RT-qPCR, remains the gold standard. Nevertheless, the approach is almost exclusively performed in large, centralized clinical laboratories, due to its extensive processing, high complexity and need for trained personnel; reliance on RT-qPCR has thus placed much pressure on public health systems (Huang H, et al., *ACS Nano.* 2020, 14: 3747-3754; Weissleder R et al., *Sci Transl Med.* 2020, 12, eabc1931), leading to a significant global supply shortage and delayed diagnoses. For prompt detection and efficient management, rapid and accurate diagnostic assays are urgently needed [Ong C W M et al., *Eur Respir J.* 2020, 56: 2001727; Ong C W M et al., *Int J Tubc Lung Dis.* 2020, 24:547-548]. We developed the CATCH assay as an alternative nucleic acid detection method to complement the current gold standard. Specifically, the CATCH assay demonstrates distinct advantages, through its unique assay mechanism and facile clinical adaptation, to address multiple challenges of COVID-19 diagnostics.

From the assay perspective, CATCH leverages DNA-enzyme hybrid complexes as hyper-responsive molecular switches. By tuning their molecular composition, the multi-component molecular switches are prepared in a hyper-responsive state—the transition state—that can be readily activated upon the direct hybridization of even sparse RNA targets to turn on substantial enzymatic activity. CATCH thus achieves an enhanced response that that is not only bigger in magnitude, but also faster in kinetics. Yet, CATCH retains all key advantages inherent to molecular switching: 1) it is highly specific and activates only when complementary targets bind to the switches; 2) it can be readily integrated with other enzyme cascades (e.g., HRP) for further signal enhancement; and 3) it enables programmable design and rapid new assay prototyping. CATCH achieved a LOD of 8 RNA copies per μl (>10,000-fold more sensitive than our previous platform), could be completed in <1 hour at room temperature and applied directly to a variety of sample types (e.g., swab lysates). Its superior performance enables CATCH to accurately detect SARS-CoV-2 even in patient samples with a low viral load.

For clinical adaptation, CATCH detects through target hybridization, instead of conventional target amplification (as in RT-qPCR). This enables the technology to bypass essentially all critical steps of RT-qPCR (i.e., RNA extraction, reverse transcription and thermal cycling amplification). Importantly, CATCH supports versatile assay implementation to accommodate the different diagnostic needs of COVID-19. In its 96-well format, the assay configuration closely resembles conventional ELISA in terms of assay workflow and readout, and can be readily adapted for high-throughput analysis, using existing infrastructure of clinical laboratories (e.g., plate reader and trained personnel). In its portable format, CATCH is implemented through a miniaturized microfluidic cartridge, where assay reagents are lyophilized within the device for user-friendly application and smartphone-based detection [Yelleswarapu V et al., *Proc Nat Acad Sci USA.* 2019, 116: 4489-4495; Xu H et al., *Sci Adv.* 2020, 6: eaaz7445; Wu X et al., *Sci Adv.* 2020, 6: eaba2556]. For different clinical applications, the CATCH assay threshold should be adjusted with respect to the proposed application. This threshold setting presents a trade-off between assay sensitivity vs. specificity. For example, considering the potential application of CATCH as a preliminary screening test, we prioritized assay sensitivity when setting the current detection threshold (100% sensitivity, minimal false negatives and maximal false positives); even at this assay threshold, we determined a low incidence of false positives (<8%), which is within the range reported of existing assays (0-16.7%) [Surkova E et al., *Lancet Respir Med.* 2020, 8: 1167-1168; Cohen A N et al., *medRxiv* (2020). doi.org/10.1101/2020.04.26.20080911]. The cause of false results in nucleic acid tests could be assay-associated or PCR-based misclassification, both of which have been reported [Cohen A N et al., *medRxiv* (2020). doi.org/10.1101/2020.04.26.20080911; Vogels C B F et al., *Nat Microbiol.* 2020, 5: 1299-1305].

The technology has the potential to be expanded further. For COVID-19 diagnostics, in view of the rapidly evolving pandemic, we envision the integration of multiple CATCH switches, designed to recognize different genetic loci of SARS-CoV-2, to not only enhance the detection coverage of the infection, but also enable subtype differentiation and mutation identification [Toyoshima Y et al., *J Hum Genet.* 2020, 65(12): 1075-1082]. With its robust performance in minimally-processed clinical lysates, CATCH could be readily expanded to investigate other more accessible sample types (e.g., saliva and sputum) [Garg N et al., *Lab Chip.* 2019, 19: 1524-1533; Jeong J H et al., *J Med Virol.* 2014, 86: 2122-2127]. To further improve user-friendliness, the microfluidic CATCH platform could be integrated with automated liquid handling systems (e.g., computer-programmed fluidics and pumps for compact liquid handling) [Shaffer S M et al., *Lab Chip.* 2015, 15: 3170-3182; Yeh E C et al., *Sci Adv.* 2017, 3: e1501645]. Such sample expansion and system automation could facilitate new clinical opportunities for repeat-testing as well as self-testing. Finally, beyond the current COVID-19 pandemic, CATCH can be further developed to discover and measure new biomarker signatures. The platform could be applied across a spectrum of diseases (e.g., infectious diseases, cancers and neurodegenerative diseases) to facilitate sensitive detection of nucleic acid targets and composite signatures [Lim C Z J et al., *Nat Commun.* 2019, 10: 1144]. Further technical improvements, such as multiplexed microfluidic compartmentalization [Duncombe T A et al., *Nat Rev Mol Cell Biol.* 2015, 16: 554-567; Tokeshi M et al., *Anal Chem.* 2002, 74: 1565-1571; Shao H et al., *Nat Commun.* 2015, 6: 6999], could enable microarray-type assay implementation for highly-parallel biomarker discovery and large-scale clinical validation.

REFERENCES

1. Y. Bai, L. Yao, T. Wei, F. Tian, D. Y. Jin, L. Chen, M. Wang, Presumed Asymptomatic Carrier Transmission of COVID-19. *JAMA* 323(14), 1406-1407 (2020).
2. J. P. Broughton, X. Deng, G. Yu, C. L. Fasching, V. Servellita, J. Singh, X. Miao, J. A. Streithorst, A. Granados, A. Sotomayor-Gonzalez, K. Zorn, A. Gopez, E. Hsu, W. Gu, S. Miller, C. Y. Pan, H. Guevara, D. A. Wadford, J. S. Chen, C. Y. Chiu, CRISPR-Cas12-based detection of SARS-CoV-2. *Nat Biotechnol* 38, 870-874 (2020).
3. E. A. Bruce, M. L. Huang, G. A. Perchetti, S. Tighe, P. Laaguiby, J. J. Hoffman, D. L. Gerrard, A. K. Nalla, Y. Wei, A. L. Greninger, S. A. Diehl, D. J. Shirley, D. G. B. Leonard, C. D. Huston, B. D. Kirkpatrick, J. A. Dragon, J. W. Crothers, K. R. Jerome, J. W. Botten, Direct RT-qPCR detection of SARS-CoV-2 RNA from patient nasopharyngeal swabs without an RNA extraction step. *bioRxiv* (2020). doi.org/10.1101/2020.03.20.001008.
4. L. J. Carter, L. V. Garner, J. W. Smoot, Y. Li, Q. Zhou, C. J. Saveson, J. M. Sasso, A. C. Gregg, D. J. Soares, T. R. Beskid, S. R. Jervey, C. Liu, Assay Techniques and Test Development for COVID-19 Diagnosis. *ACS Cent Sci* 6, 591-605 (2020).
5. Centers for Disease Control and Prevention, CDC 2019-Novel Coronavirus (2019-nCoV) Real-Time RT-PCR Diagnostic Panel. (2020), (available at worldwideweb-dotfda.gov/media/134922/download).
6. A. W. H. Chin, J. T. S. Chu, M. R. A. Perera, K. P. Y. Hui, H. L. Yen, M. C. W. Chan, M. Peiris, L. L. M. Poon, Stability of SARS-CoV-2 in different environmental conditions. *The Lancet Microbe* 1, el0 (2020).
7. A. N. Cohen, B. Kessel, M. G. Milgroom, Diagnosing COVID-19 infection: the danger of over-reliance on positive test results. *medRxiv* (2020). doi.org/10.1101/2020.04.26.20080911.
8. C. Dang, S. D. Jayasena, Oligonucleotide inhibitors of Taq DNA polymerase facilitate detection of low copy number targets by PCR. *J Mol Biol* 264, 268-278 (1996).

9. T. A. Duncombe, A. M. Tentori, A. E. Herr, Microfluidics: reframing biological enquiry. *Nat Rev Mol Cell Biol* 16, 554-567 (2015).
10. N. Garg, D. Boyle, A. Randall, A. Teng, J. Pablo, X. Liang, D. Camerini, A. P. Lee, Rapid immunodiagnostics of multiple viral infections in an acoustic microstreaming device with serum and saliva samples. *Lab Chip* 19, 1524-1533 (2019).
11. A. E. Gorbalenya, S. C. Baker, R. S. Baric, R. J. de Groot, C. Drosten, A. A. Gulyaeva, B. L. Haagmans, C. Lauber, A. M. Leontovich, B. W. Neuman, D. Penzar, S. Perlman, L. L. M. Poon, D. V. Samborskiy, I. A. Sidorov, I. Sola, J. Ziebuhr, Coronaviridae Study Group of the International Committee on Taxonomy of Viruses, The species Severe acute respiratory syndrome-related coronavirus: classifying 2019-nCoV and naming it SARS-CoV-2. *Nat Microbiol* 5, 536-544 (2020).
12. H. Hasegawa, N. Savory, K. Abe, K. Ikebukuro, Methods for Improving Aptamer Binding Affinity. *Molecules* 21, 421 (2016).
13. H. Huang, C. Fan, M. Li, H.-L. Nie, F.-B. Wang, H. Wang, R. Wang, J. Xia, X. Zheng, X. Zuo, J. Huang, COVID-19: A Call for Physical Scientists and Engineers. *ACS Nano* 14, 3747-3754 (2020).
14. N. R. Y. Ho, G. S. Lim, N. R. Sundah, D. Lim, T. P. Loh, H. Shao, Visual and modular detection of pathogen nucleic acids with enzyme-DNA molecular complexes. *Nat Commun* 9, 3238 (2018).
15. J. H. Jeong, K. H. Kim, S. H. Jeong, J. W. Park, S. M. Lee, Y. H. Seo, Comparison of sputum and nasopharyngeal swabs for detection of respiratory viruses. *J Med Virol* 86, 2122-2127 (2014).
16. M. R. Jones, N. C. Seeman, C. A. Mirkin, Nanomaterials. Programmable materials and the nature of the DNA bond. *Science* 347, 1260901 (2015).
17. A. Ladha, J. Joung, O. Abudayyeh, J. Gootenberg, F. Zhang, A 5-min RNA preparation method for COVID-19 detection with RT-qPCR. *medRxiv* (2020). Doi.org/10.1101/2020.05.07.20055947.
18. J. Li, A. A. Green, H. Yan, C. Fan, Engineering nucleic acid structures for programmable molecular circuitry and intracellular biocomputation. *Nat Chem* 9, 1056-1067 (2017).
19. Y. Li, Y. T. Cu, D. Luo, Multiplexed detection of pathogen DNA with DNA-based fluorescence nanobarcodes. *Nat Biotechnol* 23, 885-889 (2005).
20. Y. Li, L. Yao, J. Li, L. Chen, Y. Song, Z. Cai, C. Yang, Stability issues of RT-PCR testing of SARS-CoV-2 for hospitalized patients clinically diagnosed with COVID-19. *J Med Virol* 92, 903-908 (2020).
21. C. Z. J. Lim, Y. Zhang, Y. Chen, H. Zhao, M. C. Stephenson, N. R. Y. Ho, Y. Chen, J. Chung, A. Reilhac, T. P. Loh, C. L. H. Chen, H. Shao, Subtyping of circulating exosome-bound amyloid β reflects brain plaque deposition. *Nat Commun* 10, 1144 (2019).
22. K. Okonechnikov, O. Golosova, M. Fursov, T. UGENE, Unipro UGENE: a unified bioinformatics toolkit. *Bioinformatics* 28, 1166-1167 (2012).
23. C. W. M. Ong, G. B. Migliori, M. Raviglione, G. MacGregor-Skinner, G. Sotgiu, J. W. Alffenaar, S. Tiberi, C. Adlhoch, T. Alonzi, S. Archuleta, S. Brusin, E. Cambau, M. R. Capobianchi, C. Castilletti, R. Centis, D. M. Cirillo, L D'Ambrosio, G. Delogu, S. M. R. Esposito, J. Figueroa, J. S. Friedland, B. H. Choon Heng, G. Ippolito, M. Jankovic, H. Y. Kim, S. R. Klintz, C. Ködmön, E. Lalle, Y. S. Leo, C. C. Leung, A. G. Martson, M. Melazzini, S. Najafi Fard, P. Penttinen, L. Petrone, E. Petruccioli, E. Pontali, L. Saderi, M. Santin, A. Spanevello, R. van Crevel, M. J. van der Werf, D. Visca, M. Viveiros, J. P. Zellweger, A. Zumla, D. Goletti, Epidemic and pandemic viral infections: impact on tuberculosis and the lung. A consensus by the World Association for Infectious Diseases and Immunological Disorders (WAidid), Global Tuberculosis Network (GTN) and members # of ESCMID Study Group for Mycobacterial Infections (ESGMYC). *Eur Respir J* 56, 2001727 (2020).
24. C. W. M. Ong, D. Goletti, Impact of the global COVID-19 outbreak on the management of other communicable diseases. *Int J Tuberc Lung Dis* 24, 547-548 (2020).
25. Y. Pan, D. Zhang, P. Yang, L. L. M. Poon, Q. Wang, Viral load of SARS-CoV-2 in clinical samples. *Lancet Infect Dis* 20, 411-412 (2020).
26. C. Rothe, M. Schunk, P. Sothmann, G. Bretzel, G. Froeschl, C. Wallrauch, T. Zimmer, V. Thiel, C. Janke, W. Guggemos, M. Seilmaier, C. Drosten, P. Vollmar, K. Zwirglmaier, S. Zange, R. Wölfel, M. Hoelscher, Transmission of 2019-nCoV Infection from an Asymptomatic Contact in Germany. *N Engl J Med* 382, 970-971 (2020).
27. S. M. Shaffer, R. P. Joshi, B. S. Chambers, D. Sterken, A. G. Biaesch, D. J. Gabrieli, Y. Li, K. A. Feemster, S. E. Hensley, D. Issadore, A. Raj, Multiplexed detection of viral infections using rapid in situ RNA analysis on a chip. *Lab Chip* 15, 3170-3182 (2015).
28. H. Shao, J. Chung, K. Lee, L. Balaj, C. Min, B. S. Carter, F. H. Hochberg, X. O. Breakefield, H. Lee, R. Weissleder, Chip-based analysis of exosomal mRNA mediating drug resistance in glioblastoma. *Nat Commun* 6, 6999 (2015).
29. P. Song, J. Shen, D. Ye, B. Dong, F. Wang, H. Pei, J. Wang, J. Shi, L. Wang, W. Xue, Y. Huang, G. Huang, X. Zuo, C. Fan, Programming bulk enzyme heterojunctions for biosensor development with tetrahedral DNA framework. *Nat Commun* 11, 838 (2020).
30. N. R. Sundah, N. R. Y. Ho, G. S. Lim, A. Natalia, X. Ding, Y. Liu, J. E. Seet, C. W. Chan, T. P. Loh, H. Shao, Barcoded DNA nanostructures for the multiplexed profiling of subcellular protein distribution. *Nat Biomed Eng* 3, 684-694 (2019).
31. E. Surkova, V. Nikolayevskyy, F. Drobniewski, False-positive COVID-19 results: hidden problems and costs. *Lancet Respir Med* 8, 1167-1168 (2020).
32. M. Tokeshi, T. Minagawa, K. Uchiyama, A. Hibara, K. Sato, H. Hisamoto, T. Kitamori, Continuous-flow chemical processing on a microchip by combining microunit operations and a multiphase flow network. *Anal Chem* 74, 1565-1571 (2002).
33. Y. Toyoshima, K. Nemoto, S. Matsumoto, Y. Nakamura, K. Kiyotani, SARS-CoV-2 genomic variations associated with mortality rate of COVID-19. *J Hum Genet* (2020).
34. C. B. F. Vogels, A. F. Brito, A. L. Wyllie, J. R. Fauver, I. M. Ott, C. C. Kalinich, M. E. Petrone, A. Casanovas-Massana, M. Catherine Muenker, A. J. Moore, J. Klein, P. Lu, A. Lu-Culligan, X. Jiang, D. J. Kim, E. Kudo, T. Mao, M. Moriyama, J. E. Oh, A. Park, J. Silva, E. Song, T. Takahashi, M. Taura, M. Tokuyama, A. Venkataraman, O. E. Weizman, P. Wong, Y. Yang, N. R. Cheemarla, E. B. White, S. Lapidus, R. Earnest, B. Geng, P. Vijayakumar, C. Odio, J. Fournier, S. Bermejo, S. Farhadian, C. S. Dela Cruz, A. Iwasaki, A. I. Ko, M. L. Landry, E. F. Foxman, N. D. Grubaugh, Analytical sensitivity and efficiency comparisons of SARS-CoV-2 RT-qPCR primer-probe sets. *Nat Microbiol* 5, 1299-1305 (2020).
35. R. Weissleder, H. Lee, J. Ko, M. J. Pittet, COVID-19 diagnostics in context. *Sci Transl Med* 12, eabc1931 (2020).

36. O. I. Wilner, Y. Weizmann, R. Gill, O. Lioubashevski, R. Freeman, I. Willner, Enzyme cascades activated on topologically programmed DNA scaffolds. *Nat Nanotechnol* 4, 249-254 (2009).
37. X. Wu, H. Zhao, A. Natalia, C. Z. J. Lim, N. R. Y. Ho, C. J. Ong, M. C. C. Teo, J. B. Y. So, H. Shao, Exosome-templated nanoplasmonics for multiparametric molecular profiling. *Sci Adv* 6, eaba2556 (2020).
38. H. Xu, A. Xia, D. Wang, Y. Zhang, S. Deng, W. Lu, J. Luo, Q. Zhong, F. Zhang, L. Zhou, W. Zhang, Y. Wang, C. Yang, K. Chang, W. Fu, J. Cui, M. Gan, D. Luo, M. Chen, An ultraportable and versatile point-of-care DNA testing platform. *Sci Adv* 6, eaaz7445 (2020).
39. C. Yan, J. Cui, L. Huang, B. Du, L. Chen, G. Xue, S. Li, W. Zhang, L. Zhao, Y. Sun, H. Yao, N. Li, H. Zhao, Y. Feng, S. Liu, Q. Zhang, D. Liu, J. Yuan, Rapid and visual detection of 2019 novel coronavirus (SARS-CoV-2) by a reverse transcription loop-mediated isothermal amplification assay. *Clin Microbiol Infect* 26, 773-779 (2020).
40. E. C. Yeh, C. C. Fu, L. Hu, R. Thakur, J. Feng, L. P. Lee, Self-powered integrated microfluidic point-of-care low-cost enabling (SIMPLE) chip. *Sci Adv* 3, e1501645 (2017).
41. V. Yelleswarapu, J. R. Buser, M. Haber, J. Baron, E. Inapuri, D. Issadore, Mobile platform for rapid sub-picogram-per-milliliter, multiplexed, digital droplet detection of proteins. *Proc Natl Acad Sci* U SA 116, 4489-4495 (2019).

What is claimed is:

1. A method of detecting target polynucleotides in a sample, comprising the steps of:

(a) providing a sample comprising polynucleotides;

(b) providing a composition comprising at least one DNA polymerase enzyme, at least one enhancer, and at least one DNA polymerase inhibitor, wherein;

i) the enhancer is a polynucleotide comprising a sequence that is complementary to a target polynucleotide sequence;

ii) the DNA polymerase inhibitor is a polynucleotide comprising a conserved region and a variable region, wherein the conserved region is recognized and bound by the DNA polymerase enzyme, and the variable region is complementary to a portion of the enhancer;

iii) complementary sequences of the variable region of the inhibitor and enhancer form a duplexed inhibitory DNA complex which inhibits DNA polymerase activity;

iv) the composition comprises an amount of inhibitory complex that has been determined to have the fastest response and/or highest signal-to-noise ratio, by using first derivative of a titration curve of inhibitory complex v polymerase activity and/or by using first derivative of a titration curve of ratios of enhancer: inhibitor;

(c) contacting the sample comprising nucleic acid with the composition of (b), wherein target polynucleotide binding to:

(i) the enhancer sequence region of the duplex in (b) displaces the inhibitor, thereby releasing and activating the DNA polymerase;

(d) providing a signaling nanostructure that is reactive to active DNA polymerase enzyme from step (c);

(e) contacting the signaling nanostructure with active DNA polymerase enzyme from step (c);

(f) detecting signal development, wherein a change in the intensity of signal indicates the presence of target nucleic acid in the sample when using composition (b).

2. The method of claim 1, wherein the signaling nanostructure in d) comprises:

i) a self-priming portion responsive to the DNA polymerase enzyme, whereby in the presence of labelled oligonucleotides (dNTPs) and signal development reagents, the activated DNA polymerase enzyme adds labelled oligonucleotides to the signaling nanostructure and the signal development reagents bind to the labelled oligonucleotides incorporated into the self-primed portion; or ii) a self-priming exonuclease dumbbell nanostructure responsive to DNA polymerase enzyme exonuclease activity, wherein activated DNA polymerase enzyme removes labelled dNTPs from the dumbbell signaling nanostructure.

3. The method of claim 1, further comprising the step of:

(g) diagnosing the patient with the disease when presence of target nucleic acid in the sample is detected.

4. The method according to claim 1, wherein the DNA polymerase inhibitor conserved sequence region comprises the nucleic acid sequence set forth in SEQ ID NO: 14; 5'-CAATGTACAGTATTG-3'; and/or wherein the enhancer to inhibitor ratio in the composition is less than 1:1.

5. The method according to claim 1, wherein the enhancer is at least one nucleotide longer than the inhibitor duplex region; and/or wherein the enhancer is about 35 to 45 nucleotides in length; and/or wherein about half of the length of the enhancer oligonucleotide forms the inhibitor-enhancer duplex and about half forms an overhang segment.

6. The method according to claim 2, wherein the signaling nanostructure in d) comprises:

i) a self-priming portion comprising the nucleic acid sequence set forth in SEQ ID NO: 5: 5'-CGGCGTACGTAGAGCGTTGAGCAGGATGCCAACAGTCGATCAGGACGAGTGCTAACG CATTGTCGATAGCTCAGCTGTCTGAGCTATCGACAATGCGTT-3'; or ii) a self-priming exonuclease dumbbell nanostructure comprising the nucleic acid sequence set forth in SEQ ID NO: 6: 5'-GTGCGTACATAGATCGTTATCTGTCTAACGATCTATGTAC GCACTCACTCAGCTAACGCATTGTCGATAGCTCAGCTGTCTGAGCTATCGACAATGCGT T-3'.

7. The method according to claim 1, wherein the dNTP label is biotin; and/or wherein the signal development reagents comprise a fusion protein comprising avidin or a derivative thereof and an enzyme, selected from a group comprising but not limited to HRP, beta-lactamase, amylase, beta-galactosidase, and respective substrates selected from a group comprising but not limited to DAB, TMB, ABTS, ADHP, nitrocefin, luminol, starch and iodine, wherein signals can be measured and quantified as but not limited to colour, fluorescence, luminescence or electrochemical changes.

8. The method according to claim 1, wherein the target is at least one nucleic acid associated with a non-human or human disease, genetic variants, forensic, strain identification, environmental and/or food contamination.

9. The method according to claim 1, wherein the target is at least one pathogen polynucleotide.

10. The method according to claim 1, wherein the target is a SARS-COV-2 polynucleotide; or wherein the target is a SARS-COV-2 polynucleotide and the inhibitor and enhancer polynucleotides are selected from the group comprising SEQ ID NO: 1, SEQ ID NO: 2, SEQ ID NO: 3 and SEQ ID NO: 4.

11. The method according to claim 1, performed in a multi-well format, a microfluidic device or lateral flow device.

12. The method according to claim 1, wherein the steps are performed in the range from 16° C. to 40° C., or at room temperature.

13. A device comprising:

(i) composition b) comprising at least one DNA polymerase enzyme and at least one inhibitory DNA complex, of claim 1, at a first location;

(ii) signaling nanostructures attached at a second location; and (iii) an intermediate stage for mixing of said detection nanostructures with sample nucleic acid to release active enzyme to said second location.

14. The device of claim 13, selected from a group comprising a multi-well plate, a microfluidic device and a lateral flow device.

15. The device of claim 13, wherein the device is a microfluidic device comprising:

(i) an inlet at a first location, to introduce test sample, positive and negative controls, and reconstitute the lyophilized reagents in the device including at least one DNA polymerase enzyme, at least one enhancer, and at least one DNA polymerase inhibitor as defined in any aspect of the invention;

(ii) a detection chamber comprising signaling nanostructures at a second location, in fluid connection with said first location, to receive activated DNA polymerase enzyme;

(iii) valves between said first and second locations to control flow of sample and reagents;

wherein, when the device is assembled and in use, there is fluidic flow from the sample inlet to an outlet.

16. A nucleic acid detection kit comprising;

(a) a composition comprising at least one DNA polymerase enzyme and at least one inhibitory DNA complex, wherein the inhibitory DNA complex comprises a DNA polymerase enzyme-specific DNA inhibitor and an enhancer polynucleotide, wherein the inhibitor has a conserved sequence region and a variable sequence region, wherein the variable sequence region comprises an overhang segment which is at least 7 nucleotides complementary to, and forms a duplex with, a portion of the enhancer polynucleotide, wherein the enhancer polynucleotide is at least one nucleotide longer than the inhibitor-enhancer duplex and has more than 7 nucleotides complementary to a target polynucleotide, wherein the composition comprises an amount of inhibitory complex that has been determined to have the fastest response and/or highest signal-to-noise ratio by using first derivative of a titration curve of inhibitory complex v polymerase activity and/or by using first derivative of a titration curve of ratios of enhancer: inhibitor; and/or (b) a signaling nanostructure that is reactive to active DNA polymerase enzyme; and/or (c) labelled nucleotides (dNTPs) and signal development reagents, wherein active DNA polymerase enzyme adds labelled nucleotides to the signaling nanostructure and the signal development reagents bind to the labelled nucleotides incorporated into the self-primed portion.

17. The nucleic acid detection kit of claim 16, wherein said composition and said signaling nanostructure are as defined according to any one of the preceding claims.

18. The nucleic acid detection kit of claim 16, configured into a device comprising:

(i) composition b) comprising at least one DNA polymerase enzyme and at least one inhibitory DNA complex at a first location;

(ii) signalling nanostructures attached at a second location; and (iii) an intermediate stage for mixing of said detection nanostructures with sample nucleic acid to release active enzyme to said second location.

19. The nucleic acid detection kit of claim 16, wherein at least one of the inhibitor polynucleotides and/or enhancer polynucleotides is structurally and/or chemically modified from its natural nucleic acid.

20. The nucleic acid detection kit of claim 19, wherein said structural and/or chemical modification is selected from the group comprising the addition of tags, the addition of phosphorothioate (PS) bonds, 2'-O-Methyl modifications and/or phosphoramidite C3 Spacers during synthesis.

* * * * *